US011987542B2

(12) United States Patent
Hammock et al.

(10) Patent No.: US 11,987,542 B2
(45) Date of Patent: May 21, 2024

(54) CO-CRYSTAL OF SORAFENIB DERIVATIVES AND PROCESS FOR PREPARATION THEREOF

(71) Applicant: EicOsis, LLC, Davis, CA (US)

(72) Inventors: Bruce D. Hammock, Davis, CA (US); Sung Hee Hwang, Davis, CA (US); Karen M. Wagner, Davis, CA (US); Cynthia B. McReynolds, Davis, CA (US)

(73) Assignee: EicOsis, LLC, Davis, CA (US)

( * ) Notice: Subject to any disclaimer, the term of this patent is extended or adjusted under 35 U.S.C. 154(b) by 620 days.

(21) Appl. No.: 17/258,013

(22) PCT Filed: Jul. 3, 2019

(86) PCT No.: PCT/US2019/040583
§ 371 (c)(1),
(2) Date: Jan. 5, 2021

(87) PCT Pub. No.: WO2020/010244
PCT Pub. Date: Jan. 9, 2020

(65) Prior Publication Data
US 2021/0179549 A1 Jun. 17, 2021

Related U.S. Application Data

(60) Provisional application No. 62/694,635, filed on Jul. 6, 2018.

(51) Int. Cl.
| | | |
|---|---|---|
| *C07C 275/26* | (2006.01) | |
| *A61K 9/00* | (2006.01) | |
| *A61K 9/08* | (2006.01) | |
| *A61K 9/20* | (2006.01) | |

(Continued)

(52) U.S. Cl.
CPC .......... *C07C 275/26* (2013.01); *A61K 9/0019* (2013.01); *A61K 9/0053* (2013.01);
(Continued)

(58) Field of Classification Search
CPC ...... A61K 9/0019; A61K 9/0053; A61K 9/08; A61K 9/2072; A61K 31/198;
(Continued)

(56) References Cited

U.S. PATENT DOCUMENTS

2009/0023731 A1 1/2009 Gless, Jr. et al.
2015/0132408 A1 5/2015 Weiss et al.

FOREIGN PATENT DOCUMENTS

CN 104177308 A 12/2014
CN 105175263 A 12/2015
(Continued)

OTHER PUBLICATIONS

Liu et al. Eur. J. Pharm. Biopharm. 2016; 107:151-9. (Year: 2016).*
(Continued)

*Primary Examiner* — Matthew P Coughlin
*Assistant Examiner* — Ashli Ariana Chicks
(74) *Attorney, Agent, or Firm* — DLA Piper LLP (US)

(57) ABSTRACT

The present disclosure provides compounds for the inhibition of soluble epoxide hydrolase and associate disease conditions, as well as a method of treating or preventing disorders in a subject by inhibition of soluble epoxide hydrolase.

17 Claims, 9 Drawing Sheets

EC1728

(51) Int. Cl.
*A61K 9/28* (2006.01)
*A61K 31/198* (2006.01)

(52) U.S. Cl.
CPC .............. *A61K 9/08* (2013.01); *A61K 9/2072* (2013.01); *A61K 31/198* (2013.01); *C07B 2200/13* (2013.01); *C07C 2601/14* (2017.05); *C07C 2601/16* (2017.05)

(58) Field of Classification Search
CPC .............. C07C 275/26; C07C 2601/14; C07C 2601/16; C07B 2200/13
See application file for complete search history.

(56) References Cited

FOREIGN PATENT DOCUMENTS

| WO | WO 2008/116145 A2 | 9/2008 | |
|---|---|---|---|
| WO | WO-2012112570 A1 * | 8/2012 | ........... C07C 275/26 |
| WO | WO 2017/160861 A1 | 9/2017 | |

OTHER PUBLICATIONS

Karimi-Jafari Cryst. Growth Des. 2018, 18, 6370-6387. (Year: 2018).*

Kang et al. J. Mol. Struct. 2017,1130, 480-486. (Year: 2017).*

Dey et al. J Nat Sci Biol Med. Jul. 2010; 1(1):2-5. (Year: 2010).*

EP Extended European Search Report in European Application No. EP19831185.4, dated Mar. 14, 2022, 7 pages.

Kang et al., "Syntheses, Structure Characterization and Dissolution of Two Novel Cocrystals of Feboxostat," *J. Mol. Structure* (2017), 1130:480-486, Elsevier B.V.

Thakuria et al., "Pharmaceutical Cocrystals and Poorly Soluble Drugs," *Int. J. Pharm.* (2013), 453:101-125, Elsevier.

CN Office Action in Chinese Application No. 2019800540458, dated Jun. 2, 2022, 13 pages.

* cited by examiner

CO-CRYSTAL OF SORAFENIB DERIVATIVES AND PROCESS FOR PREPARATION THEREOF

CROSS-REFERENCE TO RELATED APPLICATIONS

This application is a 35 USC § 371 National Stage application of International Application No. PCT/US2019/040583 filed Jul. 3, 2019, now pending; which claims the benefit under 35 USC § 119(e) to U.S. application Ser. No. 62/694,635 filed Jul. 6, 2018, now expired. The disclosure of each of the prior applications is considered part of and is incorporated by reference in the disclosure of this application.

FIELD

The present disclosure relates to co-crystal of sorafenib derivatives and the process for preparation thereof. The disclosure also relates to a pharmaceutical composition comprising said co-crystal and one or more pharmaceutically acceptable carriers, excipients and diluents for the treatment of human and animal diseases.

BACKGROUND

Epoxide hydrolases (EHs) catalyze the hydrolysis of aliphatic epoxides or arene oxides to their corresponding diols by the addition of water. Some EHs play an important role in the metabolism of a variety of compounds including hormones, chemotherapeutic drugs, carcinogens, environmental pollutants, mycotoxins, and other harmful foreign compounds. There are two well-studied EHs, microsomal epoxide hydrolase (mEH, EC 3.3.2.9) and soluble epoxide hydrolase (sEH, EC3.3.2.10). These enzymes are very distantly related, have different subcellular localization, and have different but partially overlapping substrate selectivities. The soluble and microsomal EH forms are known to complement each other in degrading some plant natural products.

The major role of the sEH is in the metabolism of lipid epoxides including the metabolism of arachidonic acid, linoleic acid, and from other fatty acids some of which are endogenous chemical mediators. Epoxides of arachidonic acid (cis-epoxyeicosatrienoic acids or EETs) and other lipid epoxides are known effectors of blood pressure, and modulators of vascular permeability. The vasodilatory properties of EETs are associated with an increased open-state probability of calcium-activated potassium channels leading to hyperpolarization of the vascular smooth muscle. Hydrolysis of the EETs by sEH diminishes this activity. Hydrolysis of EETs by sEH also prevents their incorporation into coronary endothelial phospholipids, suggesting a regulation of endothelial function by sEH. It has been shown that treatment of spontaneous hypertensive rats (SHRs) with selective sEH inhibitors significantly reduces their blood pressure. In addition, it was claimed that male knockout sEH mice have significantly lower blood pressure than wild-type mice, however subsequent studies with back breeding into C57B mice demonstrated that 20-HETE levels increased compensating for the increase in plasma EETs.

The EETs have also demonstrated anti-inflammatory properties in endothelial cells. In contrast, diols derived from epoxy-linoleate (leukotoxin) perturb membrane permeability and calcium homeostasis, which results in inflammation that is modulated by nitric oxide synthase and endothelin-1. Micromolar concentrations of leukotoxin reported in association with inflammation and hypoxia and depression of mitochondrial respiration in vitro, and mammalian cardiopulmonary toxicity in vivo. Leukotoxin toxicity presents symptoms suggestive of multiple organ failure and acute respiratory distress syndrome (ARDS). In both cellular and organismal models, leukotoxin-mediated toxicity is dependent upon epoxide hydrolysis, suggesting roles for sEH in the regulation of inflammation and vascular permeability. The bioactivity of these epoxy-fatty acids suggests that inhibition of formation of the corresponding vicinal-dihydroxy-lipids may have therapeutic value, making sEH a promising pharmacological target.

1,3-disubstituted ureas, carbamates, and amides have been reported as new potent inhibitors of sEH. These compounds are competitive tight-binding nanomolar Ki inhibitors that interact stoichiometrically with purified recombinant human sEH. Based on the X-ray crystal structure, the urea-based sEH inhibitors were shown to establish strong hydrogen bonds between the urea group of the inhibitor and residues of the sEH active site, mimicking features encountered in the reaction coordinate of epoxide ring opening by this enzyme. These inhibitors efficiently reduced epoxide hydrolysis in several in vitro and in vivo models. Despite the high activity associated with these inhibitors, there exists a need for compounds possessing similar or increased activities, preferably with improved water solubility and/or pharmacokinetic properties to facilitate formulation and delivery.

SUMMARY

Disclosed herein is a compound that provides surprisingly improved water solubility and pharmacokinetics properties. In one aspect of the present disclosure, provided herein is a compound having Formula (I) or a stereoisomer thereof.

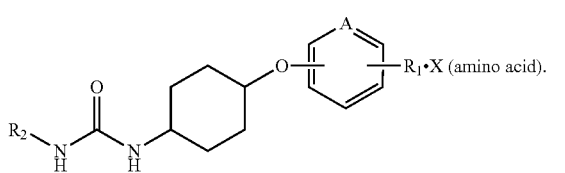

Formula (I)

A can be CH or N; $R_1$ can be —COOH or —SO$_3$H.

$R_2$ is selected from the group consisting of H, halogen, hydroxyl, $C_{1-20}$ alkyl, adamantyl group, $N_3$, $NH_2$, $NO_2$, $CF_3$, $OCF_3$, $OCHF_2$, $COC_{1-20}$alkyl, $CO_2C_{1-20}$alkyl, $C_{3-8}$cycloalkyl, $C_{3-8}$alkenyl, $C_{3-8}$alkynyl, $C_{1-10}$alkoxy, $C_{6-15}$aryl, $C_{6-15}$aryloxy, $C_{6-15}$arylthio, $C_{2-10}$carboxyl, $C_{1-10}$alkylamino, thiol, $C_{1-10}$alkyldisulfide, $C_{6-15}$arylthio, $C_{1-10}$heteroarylthio, $(C_{3-8}$cycloalkyl)thio, $C_{2-10}$heterocyclylthio, sulfonyl, $C_{1-10}$alkylsulfonyl, amido, $C_{1-10}$alkylamido, selenol, $C_{6-15}$arylselenol, $C_{1-10}$heteroarylselenol, $(C_{3-8}$cycloalkyl)selenol, C$_{2-10}$heterocyclylselenol, guanidino, C$_{1-10}$alkylguanidino, urea, C$_{1-10}$alkylurea, ammonium, C$_{1-10}$alkylammonium, cyano, C$_{1-10}$alkylcyano, nitro, C$_{1-10}$alkylnitro, adamantine, phosphonate, C$_{1-10}$alkylphosphonate, and C$_{6-15}$arylphosphonate. In some embodiments, R$_2$ can be CF$_3$, OPh or CF$_3$OPh.

Each of the above R$_2$ substituents can be optionally substituted with H, halogen, hydroxyl, N$_3$, NH$_2$, NO$_2$, CF$_3$, C$_{1-10}$alkyl, substituted C$_{1-10}$alkyl, C$_{1-10}$alkoxy, substituted C$_{1-10}$alkoxy, acyl, acylamino, acyloxy, acyl C$_{1-10}$alkyloxy, amino, substituted amino, aminoacyl, aminocarbonyl C$_{1-10}$alkyl, aminocarbonylamino, aminodicarbonylamino, aminocarbonyloxy, and aminosulfonyl.

X is an integer selected from 1-20. In some embodiments, X can be an integer selected from 1-5. In some embodiments, X can be 3. The amino acid is selected from the group consisting of glycine, L-proline, L-asparagine, L-aspartic acid, L-glutamine, L-glutamic acid, L-lysine, L-arginine, L-histidine, L-serine, L-threonine, L-cysteine, L-methionine, L-phenylalanine, L-tyrosine, L-tryptophan, L-alanine, L-valine, L-leucine, L-isoleucine, D-asparagine, D-aspartic acid, D-glutamine, D-glutamic acid, D-histidine. D-arginine, D-cysteine, D-serine, D-threonine, D-lysine, D-methionine, D-phenylalanine, D-alanine, D-valine, D-leucine, D-isoleucine and D-proline, D-tyrosine, D-tryptophan, and their derivatives with protecting groups such as BOC, Fmoc and etc.

In some embodiments, also disclosed herein is a compound having Formula (II) or a stereoisomer thereof.

N$_3$, NH$_2$, NO$_2$, CF$_3$, OCF$_3$, C$_{1-10}$alkyl, substituted C$_{1-10}$alkyl, C$_{1-10}$alkoxy, substituted C$_{1-10}$alkoxy, acyl, acylamino, acyloxy, acyl C$_{1-10}$alkyloxy, amino, substituted amino, aminoacyl, aminocarbonyl C$_{1-10}$alkyl, aminocarbonylamino, aminodicarbonylamino, aminocarbonyloxy, and aminosulfonyl.

X is an integer selected from 1-20; the amino acid is selected from the group consisting of glycine, L-proline, L-asparagine, L-aspartic acid, L-glutamine, L-glutamic acid, L-lysine, L-arginine, L-histidine, L-serine, L-threonine, L-cysteine, L-methionine, L-phenylalanine, L-tyrosine, L-tryptophan, L-alanine, L-valine, L-leucine, L-isoleucine, D-asparagine, D-aspartic acid, D-glutamine, D-glutamic acid, D-histidine. D-arginine, D-cysteine, D-serine, D-threonine, D-lysine, D-methionine, D-phenylalanine, D-alanine, D-valine, D-leucine, D-isoleucine and D-proline, D-tyrosine, D-tryptophan, and their derivatives with protecting groups such as BOC, Fmoc and etc.

In some embodiments, disclosed herein is a compound with the structure of Formula (B)

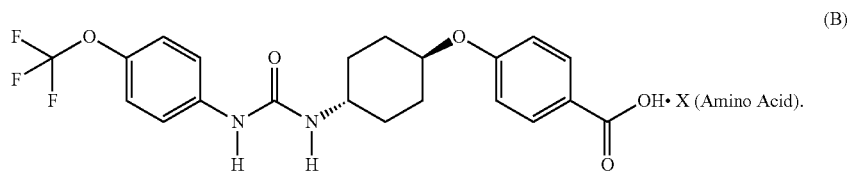

(B)

In some embodiments, disclosed herein is a compound with the structure of Formula (C)

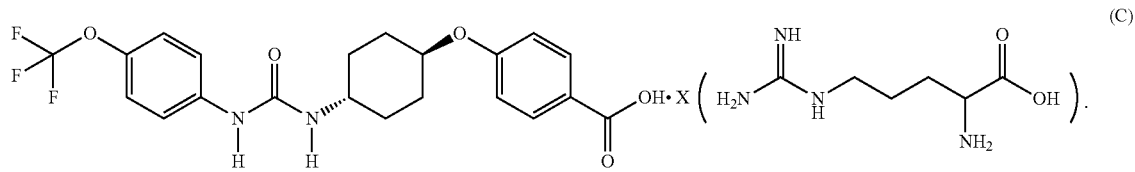

(C)

In some embodiments, the amino acid is L-arginine. In some embodiments, the disclosed co-crystal can be substantially soluble in a pharmaceutically acceptable aqueous vehicle to form an orally deliverable solution.

In some embodiments, disclosed herein is a pharmaceutical composition comprising the compound according to claim 1 having one or more pharmaceutically acceptable carriers, excipients and diluents. In some embodiments, the pharmaceutical composition can be in a form of a rapidly disintegrating tablet. In some embodiments, the pharmaceutically acceptable excipient in the pharmaceutical composition can be selected from the group consisting of surfactants, solubilizers, disintegrants, microcrystalline cellulose, starch, sodium starch glycolate, crosslinked carboxy methyl cellulose sodium, crosslinked PVP, pigments, flavors, fillers, lubricants, glidants, preservatives, thickening agents, buffering agents and pH modifiers.

In some embodiments, a process for the preparation of co-crystal of a sorafenib derivative and an amino acid is disclosed, the process includes: (a) dissolving the sorafenib derivative and the amino acid in a mixture of ethanol and water to obtain the clear solution; (b) alternatively adding Formula (II)

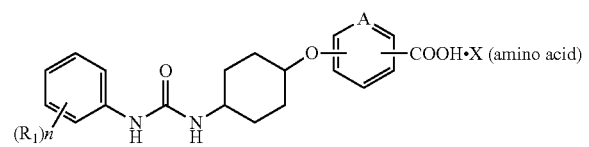

A is CH or N; n is an integer selected from 0-5; R$_1$ is selected from the group consisting of H, halogen, hydroxyl, the sorafenib derivative as a powder form in a solution of an amino acid in water and washing it with ethanol to complete dissolution; and (c) removing the water and ethanol to obtain the co-crystal.

In some embodiments, disclosed herein is a method of treating or preventing disorders in a subject by sEH inhibition, the method including (a) dissolving, in a pharmaceutically acceptable aqueous vehicle, at least one dosage unit of a pharmaceutical composition that is substantially free of water and comprises a therapeutically effective amount of co-crystal of EC1728 and L-arginine, or a pharmaceutically acceptable co-crystal thereof, and (b) orally or intravenously administering the solution to the subject before substantial.

In some embodiments, disclosed herein is a method of treating or preventing a disease or disorder in a subject by inhibiting sEH. The method includes administering to the subject a pharmaceutical composition comprising: (a) a compound of the disclosure; and (b) a pharmaceutically acceptable carrier. In embodiments, the compound is a co-crystal of EC1728 and L-arginine.

In some embodiments, disclosed herein is a method of treating or preventing a disease or disorder in a subject by inhibiting sEH. The method includes: (a) dissolving, in a pharmaceutically acceptable aqueous vehicle, a compound of the disclosure to form an aqueous pharmaceutical composition; and (b) administering the pharmaceutical composition to the subject. In embodiments, the compound is a co-crystal of EC1728 and L-arginine.

In various embodiments, the disease or disorder is renal, hepatic, or pulmonary hypertension, chronic pain, acute pain, inflammation, renal inflammation, hepatic inflammation, vascular inflammation, and lung inflammation, adult respiratory distress syndrome, diabetic complications, end stage renal disease, Raynaud syndrome, arthritis, myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Guillain Bane Syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies and neuronal ceroid lipofuscinosis.

In some embodiments, a process for the preparing a co-crystal compounds of the disclosure is provided. The process includes: (a) dissolving a sorafenib derivative and an amino acid in a mixture of ethanol and water to obtain a solution; and (b) removing the water and ethanol to obtain a co-crystal.

In some embodiments, a process for the preparing a co-crystal compound of the disclosure is provided. The process includes: (a) adding a sorafenib derivative in a dried form to a solution of an amino acid and water and washing it with ethanol to complete dissolution; and (b) removing the water and ethanol to obtain a co-crystal.

DESCRIPTION

Figure 1A:
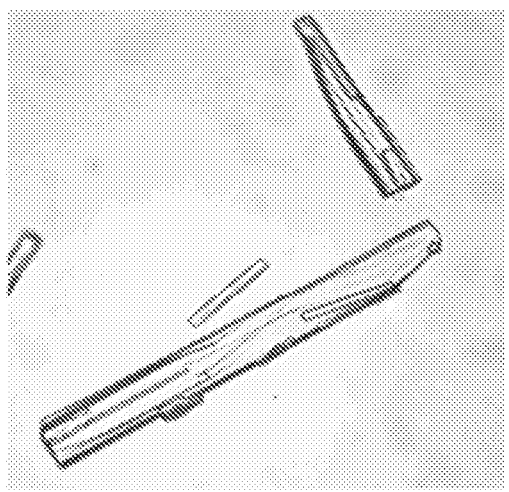
FIG. 1A shows morphology of EC1728 compound.

Disclosed herein are co-crystals of sorafenib derivatives with amino acids. In some embodiments, the co-crystals have improved water solubility and pharmacokinetic properties to facilitate formulation and delivery.

The following explanations of terms and methods are provided to better describe the present disclosure and to guide those of ordinary skill in the art in the practice of the present disclosure. The singular terms "a," "an," and "the" include plural referents unless context clearly indicates otherwise. Similarly, the word "or" is intended to include "and" unless the context clearly indicates otherwise. The term "comprises" means "includes." Thus, "comprising A or B," means "including A, B, or A and B," without excluding additional elements. The term "about" will be understood by persons of ordinary skill in the art. Whether the term "about" is used explicitly or not, every quantity given herein refers to the actual given value, and it is also meant to refer to the approximation to such given value that would be reasonably inferred based on the ordinary skill in the art.

It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless indicated otherwise, the nomenclature of substituents that are not explicitly defined herein are arrived at by naming the terminal portion of the functionality followed by the adjacent functionality toward the point of attachment. A person of ordinary skill in the art would recognize that the above definitions are not intended to include impermissible substitution patterns (e.g., methyl substituted with 5 different groups, pentavalent carbon, and the like). Such impermissible substitution patterns are easily recognized by a person of ordinary skill in the art. All publications, patent applications, patents, and other references mentioned herein are incorporated by reference in their entirety. All sequences provided in the disclosed Genbank Accession numbers are incorporated herein by reference as available on Aug. 11, 2011. In case of conflict, the present specification, including explanations of terms, will control. In addition, the materials, methods, and examples are illustrative only and not intended to be limiting.

"Soluble epoxide hydrolase" ("sEH") is an enzyme which in endothelial, smooth muscle and other cell types converts EETs to the corresponding diol compounds called dihydroxyeicosatrienoic acids ("DHETs"). The cloning and sequence of the murine sEH is set forth in Grant et al., *J. Biol. Chem.* 268(23):17628-17633 (1993). The cloning, sequence, and accession numbers of the human sEH sequence are set forth in Beetham et al., *Arch. Biochem. Biophys.* 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., *DNA Cell Biol.* 14(1): 61-71 (1995). Soluble epoxide hydrolase represents a single highly conserved gene product with over 90% homology between rodent and human (Arand et al., *FEBS Lett,* 338: 251-256 (1994)).

The term "modulate" refers to the ability of a compound to increase or decrease the function, or activity, of the associated activity (e.g., soluble epoxide hydrolase). "Modulation", as used herein in its various forms, is meant to include antagonism and partial antagonism of the activity associated with sEH. Inhibitors of sEH are compounds that, e.g., bind to, partially or totally block the enzyme's activity.

As used herein, the term "sEH-mediated disease or condition" and the like refers to a disease or condition characterized by less than or greater than normal, sEH activity. A sEH-mediated disease or condition is one in which modulation of sEH results in some effect on the underlying condition or disease (e.g., a sEH inhibitor or antagonist results in some improvement in patient well-being in at least some patients).

As used herein, the term "kinase-mediated disease or condition" and the like refers to a disease or condition characterized by less than or greater than normal, kinase activity. A kinase-mediated disease or condition is one in which modulation of kinase results in some effect on the underlying condition or disease (e.g., a kinase inhibitor or antagonist results in some improvement in patient well-being in at least some patients).

"Cancer" refers to a class of diseases in which a group of cells display uncontrolled growth, invasion intrudes upon and destroys adjacent tissues, and/or metastasis by spreading to other locations in the body via lymph or blood. "Parenchyma" refers to the tissue characteristic of an organ, as distinguished from associated connective or supporting tissues.

"Chronic Obstructive Pulmonary Disease" or "COPD" is also sometimes known as "chronic obstructive airway disease", "chronic obstructive lung disease", and "chronic airways disease." COPD is generally defined as a disorder characterized by reduced maximal expiratory flow and slow forced emptying of the lungs. COPD is considered to encompass two related conditions, emphysema and chronic bronchitis. COPD can be diagnosed by the general practitioner using art recognized techniques, such as the patient's forced vital capacity ("FVC"), the maximum volume of air that can be forcibly expelled after a maximal inhalation. In the offices of general practitioners, the FVC is typically approximated by a 6 second maximal exhalation through a spirometer. The definition, diagnosis and treatment of COPD, emphysema, and chronic bronchitis are well known in the art and discussed in detail by, for example, Honig and Ingram, in Harrison's Principles of Internal Medicine, (Fauci et al., Eds.), 14th Ed., 1998, McGraw-Hill, New York, pp. 1451-1460 (hereafter, "Harrison's Principles of Internal Medicine").

"Emphysema" is a disease of the lungs characterized by permanent destructive enlargement of the airspaces distal to the terminal bronchioles without obvious fibrosis. "Chronic bronchitis" is a disease of the lungs characterized by chronic bronchial secretions which last for most days of a month, for three months a year, for two years. As the names imply, "obstructive pulmonary disease" and "obstructive lung disease" refer to obstructive diseases, as opposed to restrictive diseases. These diseases particularly include COPD, bronchial asthma and small airway disease.

"Small airway disease." There is a distinct minority of patients whose airflow obstruction is due, solely or predominantly to involvement of the small airways. These are defined as airways less than 2 mm in diameter and correspond to small cartilaginous bronchi, terminal bronchioles and respiratory bronchioles. Small airway disease (SAD) represents luminal obstruction by inflammatory and fibrotic changes that increase airway resistance. The obstruction may be transient or permanent.

The "interstitial lung diseases (ILDs)" are a group of conditions involving the alveolar walls, perialveolar tissues, and contiguous supporting structures. As discussed on the website of the American Lung Association, the tissue between the air sacs of the lung is the interstitium, and this is the tissue affected by fibrosis in the disease. Persons with the disease have difficulty breathing in because of the stiffness of the lung tissue but, in contrast to persons with obstructive lung disease, have no difficulty breathing out. The definition, diagnosis and treatment of interstitial lung diseases are well known in the art and discussed in detail by, for example, Reynolds, H. Y, in Harrison's Principles of Internal Medicine, supra, at pp. 1460-1466. Reynolds notes that, while ILDs have various initiating events, the immunopathological responses of lung tissue are limited and the ILDs therefore have common features.

"Idiopathic pulmonary fibrosis," or "IPF," is considered the prototype ILD. Although it is idiopathic in that the cause is not known. "Inhibition", "inhibits", "inhibiting" and "inhibitor" refer to a compound that prohibits or a method of prohibiting, a specific action or function.

As used herein, the term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. As used herein, the term alkyl, unless otherwise stated, refers to both cyclic and noncyclic groups.

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multicyclic ring systems include, but are not limited to, bicycle [4.4.0]decane, bicycle[2.2.1]heptane, spiro[2.2]pentane, and the like. (Cycloalkyl)oxy refers to —O-cycloalkyl. (Cycloalkyl)thio refers to —S-cycloalkyl. This term also encompasses oxidized forms of sulfur, such as —S(=O)-cycloalkyl, or —S(=O)$_2$-cycloalkyl.

Alkenyl groups refer to straight and branched chain and cycloalkyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Representative substituted alkenyl groups may be mono-substituted or substituted more than once, such as, but not limited to, mono-, di-, or tri-substituted. Examples of alkenyl groups include, but are not limited to, vinyl, allyl, —CH=CH(CH$_3$), —CH=C(CH$_3$)$_2$, —C(CH$_3$)=CH$_2$, cyclopentenyl, cyclohexenyl, butadienyl, pentadienyl, and hexadienyl, among others.

Alkynyl groups refer to straight and branched chain and cycloalkyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Representative substituted alkynyl groups may be mono-substituted or substituted more than once, such as, but not limited to, mono-, di-, or tri-substituted. Exemplary alkynyl groups include, but are not limited to, ethynyl, propargyl, and —C≡C(CH$_3$), among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups. Aryloxy refers to —O-aryl. Arylthio refers to —S-aryl, wherein aryl is as defined herein. This term also encompasses oxidized forms of sulfur, such as —S(=O)-aryl, or —S(=O)$_2$-aryl. Heteroaryloxy refers to —O-heteroaryl. Heteroarylthio refers to —S-heteroaryl. This term also encompasses oxidized forms of sulfur, such as —S(=O)-heteroaryl, or —S(=O)$_2$-heteroaryl.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups. Heterocyclyloxy refers to —O-heterocycyl. Heterocyclylthio refers to —S-heterocycyl. This term also encompasses oxidized forms of sulfur, such as —S(=O)-heterocyclyl, or —S(=O)$_2$-heterocyclyl.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Representative polycyclic groups may be substituted one or more times.

Halogen groups include F, Cl, Br, and I; nitro group refers to —NO$_2$; cyano group refers to —CN; isocyano group refers to —N≡C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

Thiol refers to —SH. Thiocarbonyl refers to (=S). Sulfonyl refers to —SO$_2$-alkyl, —SO$_2$-substituted alkyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclyl, and —SO$_2$-substituted heterocyclyl. Sulfonylamino refers to —NR$^a$SO$_2$alkyl, —NR$^a$SO$_2$-substituted alkyl, —NR$^a$SO$_2$cycloalkyl, —NR$^a$SO$_2$substituted cycloalkyl, —NR$^a$SO$_2$aryl, —NR$^a$SO$_2$substituted aryl, —NR$^a$SO$_2$heteroaryl, —NR$^a$SO$_2$ substituted heteroaryl, —NR$^a$SO$_2$heterocyclyl, —NR$^a$SO$_2$ substituted heterocyclyl, wherein each R$^a$ independently is as defined herein.

Carboxyl refers to —COOH or salts thereof. Carboxyester refers to —C(O)O-alkyl, —C(O)O-substituted alkyl, —C(O)O-aryl, —C(O)O-substituted aryl, —C(O)β-cycloalkyl, —C(O)O-substituted cycloalkyl, —C(O)O-heteroaryl, —C(O)O-substituted heteroaryl, —C(O)O-heterocyclyl, and —C(O)O-substituted heterocyclyl. (Carboxyester) amino refers to —NR$^a$—C(O)O-alkyl, —NR$^a$—C(O)O-substituted alkyl, —NR$^a$—C(O)O-aryl, —NR$^a$—C(O)O-substituted aryl, —NR$^a$—C(O)β-cycloalkyl, —NR$^a$—C(O)O-substituted cycloalkyl, —NR$^a$—C(O)O-heteroaryl, —NR$^a$—C(O)O-substituted heteroaryl, —NR$^a$—C(O)O-heterocyclyl, and —NR$^a$—C(O)O-substituted heterocyclyl, wherein R$^a$ is as recited herein. (Carboxyester)oxy refers to —O—C(O)O-alkyl, —O—C(O)O— substituted alkyl, —O—C(O)O-aryl, —O—C(O)O-substituted aryl, —O—C(O)β-cycloalkyl, —O—C(O)O-substituted cycloalkyl, —O—C(O)O-heteroaryl, —O—C(O)O-substituted heteroaryl, —O—C(O)O-heterocyclyl, and —O—C(O)O-substituted heterocyclyl. Oxo refers to (═O).

The terms "amine" and "amino" refer to derivatives of ammonia, wherein one of more hydrogen atoms have been replaced by a substituent which include, but are not limited to alkyl, alkenyl, aryl, and heterocyclyl groups. Carbamate groups refers to —O(C═O)NR$_1$R$_2$, where R$_1$ and R$_2$ are independently hydrogen, aliphatic groups, aryl groups, or heterocyclyl groups.

Aminocarbonyl refers to —C(═O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each R$^b$ may optionally be joined together with the nitrogen bound thereto to form a heterocyclyl or substituted heterocyclyl group, provided that both R$^b$ are not hydrogen. Aminocarbonylalkyl refers to -alkylC(═O)N(R$^b$)$_2$, wherein each R$^b$ independently is selected from hydrogen, alkyl, substituted alkyl, aryl, substituted aryl, cycloalkyl, substituted cycloalkyl, heteroaryl, substituted heteroaryl, heterocyclyl, substituted heterocyclyl. Also, each R$^b$ may optionally be joined together with the nitrogen bound thereto to form a heterocyclyl or substituted heterocyclyl group, provided that both R$^b$ are not hydrogen. Aminocarbonylamino refers to —NR$^a$C(═O)N(R$^b$)$_2$, wherein R$^a$ and each R$^b$ are as defined herein. Aminodicarbonylamino refers to —NR$^a$C(═O)C(═O)N(R$^b$)$_2$, wherein R$^a$ and each R$^b$ are as defined herein. Aminocarbonyloxy refers to —O—C(═O)N(R$^b$)$_2$, wherein each R$^b$ independently is as defined herein. Aminosulfonyl refers to —SO$_2$N(R$^b$)$_2$, wherein each R$^b$ independently is as defined herein.

Imino refers to —N═R$^c$ wherein R$^c$ may be selected from hydrogen, aminocarbonylalkyloxy, substituted aminocarbonylalkyloxy, aminocarbonylalkylamino, and substituted aminocarbonylalkylamino.

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Sorafenib derivatives of the disclosure are inhibitors of sEH. In some embodiments, the sorafenib derivative has an IC$_{50}$ of less than about 100 μM, for example, an IC$_{50}$ of less than about 75 μM, 50 μM, 25 μM, 10 μM, 1 μM, 100 nM, 10 nM or 1 nM. As appropriate, the IC$_{50}$ for inhibition of sEH is determined with respect to the sEH enzyme from the same species as the human or non-human mammal receiving the inhibitor of sEH (e.g., IC$_{50}$ for inhibition of sEH is determined with respect to the species subject to treatment, e.g., with respect to the sEH enzyme from equine, bovine, ovine, porcine, canine, feline, etc., for subjects who are equine, bovine, ovine, porcine, canine, feline, respectively).

In embodiments, the sorafenib derivative inhibits sEH without also significantly inhibiting mEH. Preferably, at concentrations of 100 μM, the sorafenib derivative inhibits sEH activity by at least 50% while not inhibiting mEH activity by more than 10%. Sorafenib derivatives of the disclosure have an IC$_{50}$ (inhibition potency or, by definition, the concentration of inhibitor which reduces enzyme activity by 50%) of less than about 100 μM. Sorafenib derivatives with an IC$_{50}$ of less than 100 μM are preferred, with an IC$_{50}$ of less than 75 μM being more preferred and, in order of increasing preference, an IC$_{50}$ of 50 μM, 40 μM, 30 μM, 25 μM, 20 μM, 15 μM, 10 μM, 5 μM, 3 μM, 2 μM, 1 μM, 100 nM, 10 nM, 1.0 nM, or even less, being still more preferred. Assays for determining sEH activity are known in the art and described elsewhere herein. The IC$_{50}$ determination of the inhibitor can be made with respect to an sEH enzyme from the species subject to treatment.

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those needing preventive measures).

The term "subject" as used herein refers to any individual or patient to which the subject methods are performed. Generally, the subject is human or a non-human mammal. Illustrative non-human mammals who can benefit from the present methods include, e.g., Equidae (e.g., horse, ass, zebra), Bovidae (e.g., cattle, bison, sheep, goat, yak, impala, antelope, hartebeest, wildebeest, gnu, gazelle, water buffalo, duiker), Cervidae (e.g., deer, elk, moose, reindeer, pudu, bororo, brocket, guemal, muntjac), Suidae (e.g., pig, hog, boar), Canidae (domesticated dog, wolf, fox, coyote, jackel), Felidae (e.g., domesticated cat, cheetah, ocelot, lynx, bobcat, mountain lion, leopard, puma, lion, jaguar, tiger), Rodentia (e.g., mouse, rat, guinea pig, chinchilla, agouti, porcupine, beaver, gopher), Lagomorpha (e.g., rabbit, jackrabbit, hare, pika), Camelidae (e.g., camel, llama, alpaca, guanaco, vicugna), Ursidae (e.g., bear, panda), Procyonidae (e.g., raccoon, coati, olingo), Mustelidae (polecat, weasel, ferret, mink, fisher, badger, otter, wolverine, marten, sable, ermine), Elephantidae (e.g., elephant), rhinoceros, hippopotamus and non-human primates (e.g., chimpanzee, bonobo, macaque, ape).

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. Such amount should be sufficient to inhibit sEH activity.

Also disclosed herein are pharmaceutical compositions including compounds with the structures of Formula (I). The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable carriers that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as a-tocopherol, polyethyleneglycol 1000 succinate, or other similar polymeric delivery matrices.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The compounds of this disclosure may be employed in a conventional manner for controlling the disease described herein, including, but not limited to, renal, hepatic, or pulmonary hypertension, chronic pain, acute pain, inflammation, renal inflammation, hepatic inflammation, vascular inflammation, and lung inflammation, adult respiratory distress syndrome, diabetic complications, end stage renal disease, Raynaud syndrome, arthritis, myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Guillain Bane Syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies and neuronal ceroid lipofuscinosis. Such methods of treatment, their dosage levels and requirements may be selected by those of ordinary skill in the art from available methods and techniques.

Alternatively, the compounds of this disclosure may be used in compositions and methods for treating or protecting individuals against the diseases described herein, including, but not limited to, renal, hepatic, or pulmonary hypertension, chronic pain, acute pain, inflammation, renal inflammation, hepatic inflammation, vascular inflammation, and lung inflammation, adult respiratory distress syndrome, diabetic complications, end stage renal disease, Raynaud syndrome, arthritis, myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Guillain Bane Syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies and neuronal ceroid lipofuscinosis, over extended periods of time. The compounds may be employed in such compositions either alone or together with other compounds of this disclosure in a manner consistent with the conventional utilization of such compounds in pharmaceutical compositions. For example, a compound of this disclosure may be combined with pharmaceutically acceptable adjuvants conventionally employed in vaccines and administered in prophylactically effective amounts to protect individuals over an extended period of time against the diseases described herein.

The present disclosure is based, in part, on the discovery that inhibitors of sEH are efficacious in alleviating, reducing, inhibiting and preventing pain and/or inflammation in humans or non-human mammals, particularly painful and inflammatory conditions that could not be effectively treated using currently employed medications (e.g., non-steroidal anti-inflammatory drugs and/or analgesics were inefficacious), and/or in non-human mammals (e.g., felines, canines) in whom currently employed medications (e.g., non-steroidal anti-inflammatory drugs and/or analgesics) are toxic.

The present methods find use in preventing, reducing, inhibiting and/or reversing pain and/or inflammation in a non-human mammal. In various embodiments, the non-human mammal is an ungulate, e.g., equine, bovine, ovine or porcine. In some embodiments, the non-human mammal is canine or feline.

In various embodiments, the methods find use in providing relief from pain and/or inflammation in humans or non-human mammals who have received an inefficacious course of treatment for a painful and/or inflamed lesion (e.g., administration of a regime of non-steroidal anti-inflammatory drugs (NSAIDS) or another currently used medication was inefficacious). Inflammatory conditions in non-human animals that can be prevented, reduced, alleviated and/or mitigated by administration of an inhibitor of sEH include without limitation injury or trauma, osteopathic conditions (joint inflammation, panosteitis, osteoarthritis, hip dysplasia), allergic reactions, blockages in the lymphatic system, high blood pressure, heart failure, thyroid disease, liver disease, inflammatory bowel disease, pancreatic inflammation, and chronic kidney disease. The inflammation may be acute or chronic.

In various embodiments, the methods find use in providing relief from pain and/or inflammation for humans or non-human mammals who cannot tolerate therapeutically effective doses of NSAIDs or other active agents other than an inhibitor of sEH for the treatment of pain and/or inflammation (e.g., due to toxicity and/or an inability to metabolize currently available medications). For example, in some embodiments, the humans or non-human mammal received a course of treatment of one or more NSAIDs, as sole active agent or in combination with another active agent other than an inhibitor of sEH, and the course of treatment of one or more NSAIDs did not result in the prevention, reduction, inhibition or reversal of the inflammatory and/or neuropathic pain condition. In some embodiments, an effective regime of one or more NSAIDs cannot be administered to the human or non-human animal (e.g., would be toxic), and other active agents (that are not an NSAID and are not an inhibitor of sEH) are ineffective in providing the non-human mammal with relief from the painful and/or inflammatory condition. In some embodiments, the humans or non-human mammal has a painful and/or inflammatory condition that could not be effectively prevented, reduced, inhibited and/or reversed by administration of a NSAID co-administered with a gamma-aminobutyric acid (GABA) analog (e.g., gabapentin or pregabalin, or analogs or pro-drugs thereof).

In some embodiments, the subject mammal suffers from tendonitis or arthritis. In some embodiments, the subject suffers from a chronic inflammatory condition with a neuropathic pain component. Inflammatory pain that has not been treated successfully can evolve into a more chronic pain condition which remains even if the inflammation is resolved. Such chronic or neuropathic pain cannot be effectively reduced, inhibited or reversed by administration of NSAIDS but can be effectively reduced, inhibited or reversed by administration of an inhibitor of sEH as a sole active agent, or coadministered with another anti-inflammatory and/or analgesic agent (e.g., a therapeutic or sub-therapeutic amount of an NSAID and/or a gamma-aminobutyric acid (GABA) analog (e.g., gabapentin or pregabalin, or analogs or pro-drugs thereof).

In some embodiments, the non-human mammal is an ungulate and suffers from laminitis. Laminitis is a severely debilitating, excruciatingly painful, and life-threatening disease of the soft tissues of the foot of an ungulate, particularly the foot of an equine. Although laminitis has traditionally been viewed as an inflammatory disease, the disorder is far more complex than a simple inflammatory process. The equine foot, complex in both anatomy and physiology, integrates multiple organ systems, including the musculoskeletal, integumentary, nervous, immune, gastrointestinal and cardiovascular systems. Thus, the similarities that are often encountered between animal and human diseases do not occur with equine laminitis. The mode of weight bearing in horses, for example, is fundamentally different from that which occurs in the plantigrade foot. Equines are also unique among ungulates (i.e., cattle, sheep, goats, pigs, etc.) regarding the susceptibility to laminitis. Notwithstanding having structurally similar digit as equines, other ungulates are either not susceptible to laminitis or it occurs to a much lesser degree. Not surprisingly, the precise mechanism underlying laminitic pain remains unclear yet pain control is the single most important task in the clinical management of laminitic horses. Approximately 75% of horses afflicted with laminitis are euthanized due to the seriousness of the disease coupled with lack of efficacious therapies, especially currently available analgesics. Consequently, laminitis is widely considered as one of the most important diseases of horses and a global welfare problem.

Inhibitors of soluble epoxide hydrolase, have analgesic and antiinflammatory effects therapeutically relevant for preventing, reducing, inhibiting and/or reversing equine laminitis. These compounds have been extensively investigated in classic yet simple rodent models of inflammatory and neuropathic pain with very positive results. However, these compounds have not been tested in animals or humans regarding their analgesic effects in naturally occurring diseases. Naturally occurring diseases are typically more complex than animal models, and data obtained in models of disease do not always corroborate with findings in real patients. Here we report the successful use of sEH inhibitors for pain management of a horse with naturally occurring laminitis. That sEH inhibitor was efficacious in treating pain associated with such a complex disease as laminitis is a remarkable finding. It was more remarkable in that the pain was refractory to therapy with maximum clinically recommended doses of non-steroidal anti-inflammatory drugs and gabapentin. Systematic physical examinations and repeated laboratory analyzes of complete blood cell counts and serum biochemistry revealed no signs of toxicity, demonstrating that inhibitors of sEH are safe in horses and potentially in other animals. These extraordinary findings represent a notable leap in the field of pain medicine. In this case, we were treating a complex disease involving severe inflammation in a poorly vascularized area and inflammatory pain that likely had evolved into a chronic neuropathic pain condition. The horse was suffering as well from severe hypertension, which could be secondary to the severe pain.

In some embodiments, the non-human mammal suffers from tendonitis or osteoarthritis. Other painful inflammatory diseases such as osteoarthritis (OA) are highly prevalent in domestic animal species (e.g., horses, cats, dogs) and humans. The non-steroidal anti-inflammatory drugs (NSAIDs) are currently the most important class of systemic analgesics to treat OA pain in humans. However, NSAIDs have a relatively narrow safety margin and may have severe toxic side effects when recommended dosages are exceeded and/or prolonged use and/or in susceptible non-human mammals. These adverse effects include gastrointestinal ulceration, renal papillary necrosis, hepatocellular injury, and thrombosis, and are potentially lethal. Among animals, cats are exquisitely sensitive to the toxic effects of NSAIDs.

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to stroke, ischemia, Alzheimer's, ankylosing spondylitis, arthritis, osteoarthritis, rheumatoid arthritis, psoriatic arthritis, asthma atherosclerosis, Crohn's disease, colitis, dermatitis diverticulitis, fibromyalgia, hepatitis, irritable bowel syndrome, systemic lupus erythematous, nephritis, ulcerative colitis and Parkinson's disease. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topical transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutical dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticulare, subcapsular, subarachnoid, intraspinal and intrasternal, oral, sublingual buccal, rectal, vaginal, nasal ocular administrations, as well infusion, inhalation, and nebulization.

In treatment, the dose of agent optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subject's body weight. For example, depending on the type and severity of the disease, about 1 µg/kg to 15 mg/kg (e.g., 0.1-20 mg/kg) of agent is a candidate dosage for administration to the patient, whether, for example, by one or more separate administrations, or by continuous infusion. A typical daily dosage is in the range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. The progress of therapy is monitored by conventional techniques and assays.

In some embodiments, an agent is administered to patient at an effective amount (or dose) of less than about 1 µg/kg, for instance, about 0.35 to about 0.75 µg/kg or about 0.40 to about 0.60 µg/kg. In some embodiments, the dose of an agent is about 0.35 µg/kg, or about 0.40 µg/kg, or about 0.45 µg/kg, or about 0.50 µg/kg, or about 0.55 µg/kg, or about 0.60 µg/kg, or about 0.65 µg/kg, or about 0.70 µg/kg, or about 0.75 µg/kg, or about 0.80 µg/kg, or about 0.85 µg/kg, or about 0.90 µg/kg, or about 0.95 µg/kg or about 1 µg/kg. In various embodiments, the absolute dose of an agent is about 2 µg/subject to about 45 µg/subject, or about 5 to about 40, or about 10 to about 30, or about 15 to about 25 µg/subject. In some embodiments, the absolute dose of an agent is about 20 µg, or about 30 µg, or about 40 µg.

In various embodiments, the dose of an agent may be determined by the patient's body weight. For example, an absolute dose of an agent of about 2 µg for a pediatric human patient of about 0 to about 5 kg (e.g. about 0, or about 1, or about 2, or about 3, or about 4, or about 5 kg); or about 3 µg for a pediatric human patient of about 6 to about 8 kg (e.g. about 6, or about 7, or about 8 kg), or about 5 µg for a pediatric human patient of about 9 to about 13 kg (e.g. 9, or about 10, or about 11, or about 12, or about 13 kg); or about 8 µg for a pediatric human patient of about 14 to about 20 kg (e.g. about 14, or about 16, or about 18, or about 20 kg), or about 12 µg for a pediatric human patient of about 21 to about 30 kg (e.g. about 21, or about 23, or about 25, or about 27, or about 30 kg), or about 13 µg for a pediatric human patient of about 31 to about 33 kg (e.g. about 31, or about 32, or about 33 kg), or about 20 µg for an adult human patient of about 34 to about 50 kg (e.g. about 34, or about 36, or about 38, or about 40, or about 42, or about 44, or about 46, or about 48, or about 50 kg), or about 30 µg for an adult human patient of about 51 to about 75 kg (e.g. about 51, or about 55, or about 60, or about 65, or about 70, or about 75 kg), or about 45 µg for an adult human patient of greater than about 114 kg (e.g. about 114, or about 120, or about 130, or about 140, or about 150 kg).

In certain embodiments, an agent in accordance with the methods provided herein is administered subcutaneously (s.c.), intravenously (i.v.), intramuscularly (i.m.), intranasally or topically. Administration of an agent described herein can, independently, be one to four times daily or one to four times per month or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, an agent is administered about 1 to about 3 times (e.g. 1, or 2 or 3 times).

In some embodiments, the present disclosure provides a method for inhibiting a soluble epoxide hydrolase, the method including contacting the soluble epoxide hydrolase with a therapeutically effective amount of a compound of the present disclosure, thereby inhibiting the soluble epoxide hydrolase. In other embodiments, the compound further inhibits a kinase. In some other embodiments, the kinase can be Raf-1 or b-Raf.

In other embodiments, the present disclosure provides a method for monitoring the activity of a soluble epoxide hydrolase, the method including contacting the soluble epoxide hydrolase with an amount of a compound of the present disclosure sufficient to produce a detectable change in the fluorescence of the soluble epoxide hydrolase by interacting with one or more tryptophan residues present in the catalytic site of said soluble epoxide hydrolase, thereby monitoring the activity of the soluble epoxide hydrolase.

In another embodiment, the present disclosure provides a method for inhibiting a kinase, such as Raf-1 kinase, the method including contacting the kinase with a therapeutically effective amount of a compound of the present disclosure, thereby inhibiting the kinase. In some other embodiments, the kinase can be Raf-1 or b-Raf.

In some other embodiments, the present disclosure provides a method for monitoring the activity of a kinase, the method including contacting the kinase with an amount of a compound of the present disclosure sufficient to produce detectable changes in adenosine diphosphate (ADP) (luminescence spectroscopy) by the kinase thereby monitoring the activity of the kinase.

In another embodiment, the present disclosure provides a method for the simultaneous inhibition of both soluble epoxide hydrolase and a kinase by means of a single compound or by way of combining two or more compounds which inhibit both soluble epoxide hydrolase and a kinase for the treatment of human diseases, such as cancer.

In some embodiments, the present disclosure provides a method of treating cancer, the method including administering to a subject in need thereof, a therapeutically effective amount of a compound of the present disclosure, thereby treating cancer. In some embodiments, the present disclosure provides a method of treating cancer, the method including contacting cancer cells with a therapeutically effective amount of a compound of the present disclosure, thereby treating cancer. The contacting can be in vivo or in vitro. In some embodiments, the contacting is performed in vitro.

Methods of Treating Diseases Modulated by Soluble Epoxide Hydrolases.

In another aspect, the present disclosure provides methods of treating diseases, especially those modulated by soluble epoxide hydrolase (sEH). The methods generally involve administering to a subject in need of such treatment an effective amount of a compound of the present disclosure. The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the disclosure and the pharmaceutically acceptable salts thereof are administered via oral, parenteral, subcutaneous, intramuscular, intravenous or topical routes. Generally, the compounds are administered in dosages ranging from about 2 mg up to about 2,000 mg per day, although variations will necessarily occur depending, as noted above, on the disease target, the patient, and the route of administration. Dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated. It has previously been shown that inhibitors of soluble epoxide hydrolase ("sEH") can reduce hypertension. See, e.g., U.S. Pat. No. 6,351,506. Such inhibitors can be useful in controlling the blood pressure of persons with undesirably high blood pressure, including those who suffer from diabetes. In some embodiments, compounds of the present disclosure are administered to a subject in need of treatment for cancer, hypertension, specifically renal, hepatic, or pulmonary hypertension; inflammation, specifically renal inflammation, vascular inflammation, and lung inflammation; adult respiratory distress syndrome; diabetic complications; end stage renal disease; Raynaud syndrome and arthritis.

Methods for Inhibiting Progression of Kidney Deterioration (Nephropathy) and Reducing Blood Pressure.

In another aspect of the disclosure, the compounds of the disclosure can reduce damage to the kidney, and especially damage to kidneys from diabetes, as measured by albuminuria. The compounds of the disclosure can reduce kidney deterioration (nephropathy) from diabetes even in individuals who do not have high blood pressure. The conditions of therapeutic administration are as described above. cis-Epoxyeicosantrienoic acids ("EETs") can be used in conjunction with the compounds of the disclosure to further reduce kidney damage. EETs, which are epoxides of arachidonic acid, are known to be effectors of blood pressure, regulators of inflammation, and modulators of vascular permeability. Hydrolysis of the EETs by sEH diminishes this activity. Inhibition of sEH raises the level of EETs since the rate at which the EETs are hydrolyzed into DHETs is reduced. Without wishing to be bound by theory, it is believed that raising the level of EETs interferes with damage to kidney cells by the microvasculature changes and other pathologic effects of diabetic hyperglycemia. Therefore, raising the EET level in the kidney is believed to protect the kidney from progression from microalbuminuria to end stage renal disease. EETs are well known in the art. EETs useful in the methods of the present disclosure include 14,15-EET, 8,9-EET and 11,12-EET, and 5,6-EETs, in that order of preference. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.). EETs produced by the endothelium have anti-hypertensive properties and the EETs 11,12-EET and 14,15-EET may be endothelium-derived hyperpolarizing factors (EDHFs). Additionally, EETs such as 11,12-EET have profibrinolytic effects, anti-inflammatory actions and inhibit smooth muscle cell proliferation and migration. In the context of the present disclosure, these favorable properties are believed to protect the vasculature and organs during renal and cardiovascular disease states.

It is now believed that sEH activity can be inhibited sufficiently to increase the levels of EETs and thus augment the effects of administering sEH inhibitors by themselves. This permits EETs to be used in conjunction with one or more sEH inhibitors to reduce nephropathy in the methods of the disclosure. It further permits EETs to be used in conjunction with one or more sEH inhibitors to reduce hypertension, or inflammation, or both. Thus, medicaments of EETs can be made which can be administered in conjunction with one or more so sEH inhibitors, or a medicament containing one or more sEH inhibitors can optionally contain one or more EETs.

The EETs can be administered concurrently with the sEH inhibitor, or following administration of the sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs are administered after the inhibitor is administered, therefore, it is desirable that the EETs be administered during the period during which the inhibitor will be present in amounts to be effective to delay hydrolysis of the EETs. Typically, the EET or EETs will be administered within 48 hours of administering an sEH inhibitor. Preferably, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor.

In some embodiments, the EETs, the compound of the disclosure, or both, are provided in a material that permits them to be released over time to provide a longer duration of action. Slow release coatings are well known in the pharmaceutical art; the choice of the particular slow release coating is not critical to the practice of the present disclosure.

EETs are subject to degradation under acidic conditions. Thus, if the EETs are to be administered orally, it is desirable that they are protected from degradation in the stomach. Conveniently, EETs for oral administration may be coated to permit them to passage the acidic environment of the stomach into the basic environment of the intestines. Such coatings are well known in the art. For example, aspirin coated with so called "enteric coatings" is widely available commercially. Such enteric coatings may be used to protect EETs during passage through the stomach. An exemplary coating is set forth in the Examples.

While the anti-hypertensive effects of EETs have been recognized, EETs have not been administered to treat hypertension because it was thought endogenous sEH would hydrolyze the EETs too quickly for them to have any useful effect. Surprisingly, it was found during the course of the studies underlying the present disclosure that exogenously administered inhibitors of sEH succeeded in inhibiting sEH sufficiently that levels of EETs could be further raised by the administration of exogenous EETs. These findings underlie the co-administration of sEH inhibitors and of EETs described above with respect to inhibiting the development and progression of nephropathy. This is an important improvement in augmenting treatment. While levels of endogenous EETs are expected to rise with the inhibition of sEH activity caused by the action of the sEH inhibitor, and therefore to result in at least some improvement in symptoms or pathology, it may not be sufficient in all cases to inhibit progression of kidney damage fully or to the extent intended. This is particularly true where the diseases or other factors have reduced the endogenous concentrations of EETs below those normally present in healthy individuals. Administration of exogenous EETs in conjunction with a sEH inhibitor is therefore expected to be beneficial and to augment the effects of the sEH inhibitor in reducing the progression of diabetic nephropathy.

The present disclosure can be used with regard to any and all forms of diabetes to the extent that they are associated with progressive damage to the kidney or kidney function. The chronic hyperglycemia of diabetes is associated with long term damage, dysfunction, and failure of various organs, especially the eyes, kidneys, nerves, heart, and blood vessels. The long-term complications of diabetes include retinopathy with potential loss of vision; nephropathy leading to renal failure; peripheral neuropathy with risk of foot ulcers, amputation, and Charcot joints.

In addition, persons with metabolic syndrome are at high risk of progression to type 2 diabetes, and therefore at higher risk than average for diabetic nephropathy. It is therefore desirable to monitor such individuals for microalbuminuria, and to administer a sEH inhibitor and, optionally, one or more EETs, as an intervention to reduce the development of nephropathy. The practitioner may wait until microalbuminuria is seen before beginning the intervention. As noted above, a person can be diagnosed with metabolic syndrome without having a blood pressure of 130/85 or higher. Both persons with blood pressure of 130/85 or higher and persons with blood pressure below 130/85 can benefit from the administration of sEH inhibitors and, optionally, of one or more EETs, to slow the progression of damage to their kidneys. In some embodiments, the person has metabolic syndrome and blood pressure below 130/85.

Dyslipidemia or disorders of lipid metabolism is another risk factor for heart disease. Such disorders include an increased level of LDL cholesterol, a reduced level of HDL cholesterol, and an increased level of triglycerides. An increased level of serum cholesterol, and especially of LDL cholesterol, is associated with an increased risk of heart disease. The kidneys are also damaged by such high levels. It is believed that high levels of triglycerides are associated with kidney damage. In particular, levels of cholesterol over 200 mg/dL, and especially levels over 225 mg/dL, would suggest that sEH inhibitors and, optionally, EETs, should be administered. Similarly, triglyceride levels of more than 215 mg/dL, and especially of 250 mg/dL or higher, would indicate that administration of sEH inhibitors and, optionally, of EETs, would be desirable. The administration of compounds of the present disclosure with or without the EETs, can reduce the need to administer statin drugs (HMG-CoA reductase inhibitors) to the patients, or reduce the amount of the statins needed. In some embodiments, candidates for the methods, uses and compositions of the disclosure have triglyceride levels over 215 mg/dL and blood pressure below 130/85. In some embodiments, the candidates have triglyceride levels over 250 mg/dL and blood pressure below 130/85. In some embodiments, candidates for the methods, uses and compositions of the disclosure have cholesterol levels over 200 mg/dL and blood pressure below 130/85. In some embodiments, the candidates have cholesterol levels over 225 mg/dL and blood pressure below 130/85.

Methods of Inhibiting the Proliferation of Vascular Smooth Muscle Cells.

In other embodiments, compounds of the present disclosure inhibit proliferation of vascular smooth muscle (VSM) cells without significant cell toxicity, (e.g., specific to VSM cells). Because VSM cell proliferation is an integral process in the pathophysiology of atherosclerosis, these compounds are suitable for slowing or inhibiting atherosclerosis. These compounds are useful to subjects at risk for atherosclerosis, such as individuals who have had a heart attack or a test result showing decreased blood circulation to the heart. The conditions of therapeutic administration are as described above.

The methods of the disclosure are particularly useful for patients who have had percutaneous intervention, such as angioplasty to reopen a narrowed artery, to reduce or to slow the narrowing of the reopened passage by restenosis. In some embodiments, the artery is a coronary artery. The compounds of the disclosure can be placed on stents in polymeric coatings to provide a controlled localized release to reduce restenosis. Polymer compositions for implantable medical devices, such as stents, and methods for embedding agents in the polymer for controlled release, are known in the art and taught, for example, in U.S. Pat. Nos. 6,335,029; 6,322,847; 6,299,604; 6,290,722; 6,287,285; and 5,637,113. In some embodiments, the coating releases the inhibitor over a period of time, preferably over a period of days, weeks, or months. The particular polymer or other coating chosen is not a critical part of the present disclosure.

The methods of the disclosure are useful for slowing or inhibiting the stenosis or restenosis of natural and synthetic vascular grafts. As noted above in connection with stents, desirably, the synthetic vascular graft comprises a material which releases a compound of the disclosure over time to slow or inhibit VSM proliferation and the consequent stenosis of the graft. Hemodialysis grafts are a particular embodiment. In addition to these uses, the methods of the disclosure can be used to slow or to inhibit stenosis or restenosis of blood vessels of persons who have had a heart attack, or whose test results indicate that they are at risk of a heart attack.

In one group of embodiments, compounds of the disclosure are administered to reduce proliferation of VSM cells in persons who do not have hypertension. In another group of embodiments, compounds of the disclosure are used to reduce proliferation of VSM cells in persons who are being treated for hypertension, but with an agent that is not an sEH inhibitor.

The compounds of the disclosure can be used to interfere with the proliferation of cells which exhibit inappropriate cell cycle regulation. In one important set of embodiments, the cells are cells of a cancer. The proliferation of such cells can be slowed or inhibited by contacting the cells with a compound of the disclosure. The determination of whether a particular compound of the disclosure can slow or inhibit the proliferation of cells of any particular type of cancer can be determined using assays routine in the art.

In addition to the use of the compounds of the disclosure, the levels of EETs can be raised by adding EETs. VSM cells contacted with both an EET and a compound of the disclosure exhibited slower proliferation than cells exposed to either the EET alone or to the a compound of the disclosure alone. Accordingly, if desired, the slowing or inhibition of VSM cells of a compound of the disclosure can be enhanced by adding an EET along with a compound of the disclosure. In the case of stents or vascular grafts, for example, this can conveniently be accomplished by embedding the EET in a coating along with a compound of the disclosure so that both are released once the stent or graft is in position.

Methods of Inhibiting the Progression of Obstructive Pulmonary Disease, Interstitial Lung Disease, or Asthma. Disclosure Chronic obstructive pulmonary disease, or COPD, encompasses two conditions, emphysema and chronic bronchitis, which relate to damage caused to the lung by air pollution, chronic exposure to chemicals, and tobacco smoke. Emphysema as a disease relates to damage to the alveoli of the lung, which results in loss of the separation between alveoli and a consequent reduction in the overall surface area available for gas exchange. Chronic bronchitis relates to irritation of the bronchioles, resulting in excess production of mucin, and the consequent blocking by mucin of the airways leading to the alveoli. While persons with emphysema do not necessarily have chronic bronchitis or vice versa, it is common for persons with one of the conditions to also have the other, as well as other lung disorders.

Some of the damage to the lungs due to COPD, emphysema, chronic bronchitis, and other obstructive lung disorders can be inhibited or reversed by administering inhibitors of the enzyme known as soluble epoxide hydrolase, or "sEH". The effects of sEH inhibitors can be increased by also administering EETs. The effect is at least additive over administering the two agents separately, and may indeed be synergistic.

The studies reported herein show that EETs can be used in conjunction with sEH inhibitors to reduce damage to the lungs by tobacco smoke or, by extension, by occupational or environmental irritants. These findings indicate that the coadministration of sEH inhibitors and of EETs can be used to inhibit or slow the development or progression of COPD, emphysema, chronic bronchitis, or other chronic obstructive lung diseases which cause irritation to the lungs.

Animal models of COPD and humans with COPD have elevated levels of immunomodulatory lymphocytes and neutrophils. Neutrophils release agents that cause tissue damage and, if not regulated, will over time have a destructive effect. Without wishing to be bound by theory, it is believed that reducing levels of neutrophils reduces tissue damage contributing to obstructive lung diseases such as COPD, emphysema, and chronic bronchitis. Administration of sEH inhibitors to rats in an animal model of COPD resulted in a reduction in the number of neutrophils found in the lungs. Administration of EETs in addition to the sEH inhibitors also reduced neutrophil levels. The reduction in neutrophil levels in the presence of sEH inhibitor and EETs was greater than in the presence of the sEH inhibitor alone.

While levels of endogenous EETs are expected to rise with the inhibition of sEH activity caused by the action of the sEH inhibitor, and therefore to result in at least some improvement in symptoms or pathology, it may not be sufficient in all cases to inhibit progression of COPD or other pulmonary diseases. This is particularly true where the diseases or other factors have reduced the endogenous concentrations of EETs below those normally present in healthy individuals. Administration of exogenous EETs in conjunction with an sEH inhibitor is therefore expected to augment the effects of the sEH inhibitor in inhibiting or reducing the progression of COPD or other pulmonary diseases.

In addition to inhibiting or reducing the progression of chronic obstructive airway conditions, the disclosure also provides new ways of reducing the severity or progression of chronic restrictive airway diseases. While obstructive airway diseases tend to result from the destruction of the lung parenchyma, and especially of the alveoli, restrictive diseases tend to arise from the deposition of excess collagen in the parenchyma. These restrictive diseases are commonly referred to as "interstitial lung diseases", or "ILDs", and include conditions such as idiopathic pulmonary fibrosis. The methods, compositions and uses of the disclosure are useful for reducing the severity or progression of ILDs, such as idiopathic pulmonary fibrosis. Macrophages play a significant role in stimulating interstitial cells, particularly fibroblasts, to lay down collagen. Without wishing to be bound by theory, it is believed that neutrophils are involved in activating macrophages, and that the reduction of neutrophil levels found in the studies reported herein demonstrates that the methods and uses of the disclosure will also be applicable to reducing the severity and progression of ILDs.

In some embodiments, the ILD is idiopathic pulmonary fibrosis. In other embodiments, the ILD is one associated with an occupational or environmental exposure. Exemplars of such ILDs, are asbestosis, silicosis, coal worker's pneumoconiosis, and berylliosis. Further, occupational exposure to any of a number of inorganic dusts and organic dusts is believed to be associated with mucus hypersecretion and respiratory disease, including cement dust, coke oven emissions, mica, rock dusts, cotton dust, and grain dust (for a more complete list of occupational dusts associated with these conditions, see Table 254-1 of Speizer, "Environmental Lung Diseases," Harrison's Principles of Internal Medicine, infra, at pp. 1429-1436). In other embodiments, the ILD is sarcoidosis of the lungs. ILDs can also result from radiation in medical treatment, particularly for breast cancer, and from connective tissue or collagen diseases such as rheumatoid arthritis and systemic sclerosis. It is believed that the methods, uses and compositions of the disclosure can be useful in each of these interstitial lung diseases.

In another set of embodiments, the disclosure is used to reduce the severity or progression of asthma. Asthma typically results in mucin hypersecretion, resulting in partial airway obstruction. Additionally, irritation of the airway results in the release of mediators which result in airway obstruction. While the lymphocytes and other immunomodulatory cells recruited to the lungs in asthma may differ from those recruited as a result of COPD or an ILD, it is expected that the disclosure will reduce the influx of immunomodulatory cells, such as neutrophils and eosinophils, and ameliorate the extent of obstruction. Thus, it is expected that the administration of sEH inhibitors, and the administration of sEH inhibitors in combination with EETs, will be useful in reducing airway obstruction due to asthma.

In each of these diseases and conditions, it is believed that at least some of the damage to the lungs is due to agents released by neutrophils which infiltrate into the lungs. The presence of neutrophils in the airways is thus indicative of continuing damage from the disease or condition, while a reduction in the number of neutrophils is indicative of reduced damage or disease progression. Thus, a reduction in the number of neutrophils in the airways in the presence of an agent is a marker that the agent is reducing damage due to the disease or condition, and is slowing the further development of the disease or condition. The number of neutrophils present in the lungs can be determined by, for example, bronchoalveolar lavage.

Prophylatic and Therapeutic Methods to Reduce Stroke Damage

Inhibitors of soluble epoxide hydrolase ("sEH") and EETs administered in conjunction with inhibitors of sEH have been shown to reduce brain damage from strokes. Based on these results, we expect that inhibitors of sEH taken prior to an ischemic stroke will reduce the area of brain damage and will likely reduce the consequent degree of impairment. The reduced area of damage should also be associated with a faster recovery from the effects of the stroke.

While the pathophysiologies of different subtypes of stroke differ, they all cause brain damage. Hemorrhagic stroke differs from ischemic stroke in that the damage is largely due to compression of tissue as blood builds up in the confined space within the skull after a blood vessel ruptures, whereas in ischemic stroke, the damage is largely due to loss of oxygen supply to tissues downstream of the blockage of a blood vessel by a clot. Ischemic strokes are divided into thrombotic strokes, in which a clot blocks a blood vessel in the brain, and embolic strokes, in which a clot formed elsewhere in the body is carried through the blood stream and blocks a vessel there. But, in both hemorrhagic stroke and ischemic stroke, the damage is due to the death of brain cells. Based on the results observed in our studies, however, we would expect at least some reduction in brain damage in all types of stroke and in all subtypes.

A number of factors are associated with an increased risk of stroke. Given the results of the studies underlying the present disclosure, sEH inhibitors administered to persons with any one or more of the following conditions or risk factors: high blood pressure, tobacco use, diabetes, carotid artery disease, peripheral artery disease, atrial fibrillation, transient ischemic attacks (TIAs), blood disorders such as high red blood cell counts and sickle cell disease, high blood cholesterol, obesity, alcohol use of more than one drink a day for women or two drinks a day for men, use of cocaine, a family history of stroke, a previous stroke or heart attack, or being elderly, will reduce the area of brain damaged of a stroke. With respect to being elderly, the risk of stroke increases for every 10 years. Thus, as an individual reaches 60, 70, or 80, administration of sEH inhibitors has an increasingly larger potential benefit. As noted in the next section, the administration of EETs in combination with one or more sEH inhibitors can be beneficial in further reducing the brain damage. One can expect beneficial effects from sEHI with or without EETs in a variety of diseases which lead to ischemia reperfusion injury such as heart attacks.

In some uses and methods, the sEH inhibitors and, optionally, EETs, are administered to persons who use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

Clot dissolving agents, such as tissue plasminogen activator (TPA), have been shown to reduce the extent of damage from ischemic strokes if administered in the hours shortly after a stroke. TPA, for example, is approved by the FDA for use in the first three hours after a stroke. Thus, at least some of the brain damage from a stroke is not instantaneous, but occurs over a period of time or after a period of time has elapsed after the stroke. It is therefore believed that administration of sEH inhibitors, optionally with EETs, can also reduce brain damage if administered within 6 hours after a stroke has occurred, more preferably within 5, 4, 3, or 2 hours after a stroke has occurred, with each successive shorter interval being more preferable. Even more preferably, the inhibitor or inhibitors are administered 2 hours or less or even 1 hour or less after the stroke, to maximize the reduction in brain damage. Persons of skill are well aware of how to make a diagnosis of whether or not a patient has had a stroke. Such determinations are typically made in hospital emergency rooms, following standard differential diagnosis protocols and imaging procedures.

In some uses and methods, the sEH inhibitors and, optionally, EETs, are administered to persons who have had a stroke within the last 6 hours who: use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes. The conditions of therapeutic administration for all of these indications are as described above.

Methods of Treating Cancer

The compounds and compositions of the present disclosure are also useful in the treatment of cancer. The compounds of formula I can possess anti-proliferative activity and are therefore useful in the treatment of proliferative disorders such as cancers, leukaemias and other disorders associated with uncontrolled cellular proliferation such as psoriasis and restenosis. As defined herein, an anti-proliferative effect within the scope of the present disclosure may be demonstrated by the ability to inhibit cell proliferation in an in vitro whole cell assay, for example using any of the cell lines A549, HT29, Saos-2, HeLa or MCF-7, or by showing inhibition of a CDK enzyme (such as CDK2 or CDK4) in an appropriate assay. Using such cell line and enzymes assays it may be determined whether a compound is anti-proliferative in the context of the present disclosure.

As used herein, the term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. One of skill in the art will appreciate that other cancers and proliferative disorders can be treated by the compounds and compositions of the present disclosure. In some embodiments, the cancer is bone cancer, colon cancer, multiple myeloma, gastric cancer, colorectal cancer, prostate cancer, cervical cancer, lung cancer, pancreatic cancer, medulloblastoma, kidney cancer, liver cancer, parathyroid cancer, endometrial cancer, or breast cancer.

Kinase Inhibition. The methods of the present disclosure also include inhibition of a kinase. Any kinase can be inhibited using the compounds of the present disclosure. For example, the kinases Raf-1 and b-Raf, among others, can be inhibited by the compounds of the present disclosure.

In another aspect of the disclosure, the compounds of the disclosure can reduce the onset of cancer (carcinogenesis), primary tumor growth (cancer proliferation), and/or tumor progression (metastasis). With the advent of more complete knowledge of the molecular biology of cancer, new therapies have recently been designed which target mechanisms by which the disease escapes standard therapy. For example, the multi-kinase and VEGF-receptor inhibitors, such as sorafenib and sunitinib, interrupt the pathway by which angiogenesis becomes established and promulgated resulting in inadequate nourishment of metastatic disease thereby leading to a higher degree of treatment success. In certain malignancies, such as kidney cancer whose mechanism of oncogenesis generally involves disrupted hypoxia pathways and thus is highly angiogenic, these agents have had the effect of revolutionizing treatment. The recently described X ray-crystal structure of B-Raf complexed with sorafenib, a structural similarity between this drug and the class of urea-based compounds that inhibit the soluble epoxide hydrolase (sEH) was noted. The sEH converts epoxyeicosatrienoic acids (EETs) to the less active dihydroxyeicosatrienoic acids (DHETs). EETs are potently anti-inflammatory through mediating the nuclear factor kappa B (NF-kB) and IkB kinase system. The sEH inhibitors have been shown to stabilize the EET levels and thus have beneficial effects on hypertension, nociception, atherosclerosis, and inflammation through increasing endogenous levels of EETs and other lipid epoxides. Herein, this disclosed proposes that the simultaneous inhibition of sEH with kinases will therefore be an effective treatment for cancer.

In some embodiments, the present disclosure provides a method of treating cancer, the method including administering to a subject in need thereof, a therapeutically effective amount of a compound of the present disclosure, thereby treating cancer. In other embodiments, the present disclosure provides a method of treating cancer, the method including contacting cancer cells with a therapeutically effective amount of a compound of the present disclosure, thereby treating cancer. The contacting step can be performed either in vitro or in vivo. In some embodiments, the contacting is performed in vitro.

Table 1 below illustrates some non-limiting examples of the sorafenib derivatives used for the present disclosure.

TABLE 1

The sorafenib derivatives used for co-crystallization study in the present disclosure.

| Compound | Structure |
|---|---|
| 1471 (t-AUCB) | Adamantyl-NH-C(O)-NH-cyclohexyl-O-C6H4-COOH |
| 1686 | 4-(F3CO)-C6H4-NH-C(O)-NH-cyclohexyl-O-C6H4-COOH |
| 1728 (t-TUCB) | 4-(F3CO)-C6H4-NH-C(O)-NH-cyclohexyl-O-C6H4-COOH |
| 2084 | 4-Cl-C6H4-NH-C(O)-NH-cyclohexyl-O-C6H4-COOH |
| 2221 | 4-Cl-3-(F3C)-C6H3-NH-C(O)-NH-cyclohexyl-O-C6H4-COOH |
| 2372 | 4-(F3C)-C6H4-NH-C(O)-NH-cyclohexyl-O-C6H4-COOH |

EC1728 (formerly t-TUCB) is a compound for the treatment of both inflammatory and neuropathic pain. It was discovered at University of California, Davis as a transition-state mimic inhibitor of the soluble epoxide hydrolase (sEH, E.C. 3.3.2.10). EC1728 is a first-in-class compound to treat both inflammatory and neuropathic pain that acts by inhibiting sEH, a regulatory enzyme in the metabolism of the arachidonic acid (ARA) cascade. Arachidonic acid is one of the most abundant omega-6 fatty acids polyunsaturated fatty acid (PUFA) derived from the diet. It is stored in the cell membrane and released in response to cellular injury, inflammation or stress to act as a secondary messenger to regulate many biological processes such as wound healing and inflammation. ARA is metabolized by cyclooxygenase (COX), lipoxygenase (LOX) and cytochrome P450 (CYP450) enzymes into natural chemical mediators, termed eicosanoids. These three enzymes can equally metabolize other omega-3 and omega-6 PUFAs including omega-3 docosahexaenoic acid (DHA) and eicosapentaenoic acid (EPA). However, regardless of all these PUFAs being metabolized, this cascade is commonly referred to collectively as the ARA cascade. The ARA cascade is a major regulatory pathway and 50-75% by mass of the drugs used worldwide target this pathway. All pharmaceuticals to date modulating the ARA cascade are directed to the predominantly inflammatory cyclooxygenase (COX) and lipoxygenase (LOX) branches of the cascade. These drugs work by blocking the formation of COX and LOX metabolites that generally enhance pain and inflammation. In contrast, we are addressing the largely anti-inflammatory, but previously not exploited, CYP450 branch of the ARA cascade, where CYP450 enzymes produce regioisomers of epoxy fatty acids that reduce inflammation and inflammatory and neuropathic pain. CYP450 form regioisomers of epoxy-fatty acids from major polyunsaturated fatty acids including ARA, DHA, and EPA are abbreviated as EETs, EDPs and EEQs. The EETs (as well as EDPs and EEQs from omega-3 fatty acids, DHA and EPA) are maintained at low nanomolar levels in vivo by rapid hydration catalyzed by the sEH which converts them into far less active or even proinflammatory product diols termed DHETs. By inhibiting the sEH with pharmacological enzyme inhibitors, the levels of epoxy-fatty acids, such as EETs, which in turn reduce inflammation and pain, are increased. Approximately 90% of the degradation of EETs is by the sEH; thus, inhibiting sEH increases the desirable EETs and other epoxy-fatty acids like EDPs. There are multiple lines of evidence that the sEH is the target of sEH inhibitors in vivo and that inhibiting the enzyme raises the levels of epoxy-fatty acids, specifically EETs and EDPs. EC1728 is a potent inhibitor of the sEH in human and other animal species.

TABLE 2

Comparison of potencies of EC1728 for sEH from various animal species. $IC_{50}$ (nM)

| Human sEH[a] | Horse sEH[b] | Mouse sEH[a] | Rat sEH[a] | Dog sEH[b] | Cat sEH[b] | Rabbit sEH[b] | Pig sEH[b] | Sheep sEH[b] |
|---|---|---|---|---|---|---|---|---|
| 0.5 | 0.5 | 11 | 16 | 1.7 | 0.5 | 2 | 29 | 6 |

[a]measured with fluorescent assay.
[b]measured with radioactive assay and liver cytosolic preparation.

EC1728 is chemically known as trans-4-{4-[3-(4-trifluoromethoxy-phenyl)-ureido]-cyclohexyloxy}-benzoic acid of Formula (A) and is abbreviated as t-TUCB.

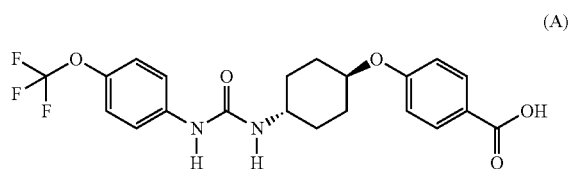 [SMILES: O=C(Nc1ccc(OC(F)(F)F)cc1)N[C@H]1CC[C@H](Oc2ccc(C(=O)O)cc2)CC1]

(A)

WO 2008/116145 A2 first discloses EC1728 and other novel urea and thiourea compounds as sEH inhibitors and their use as agents for treating a variety of sEH mediated diseases, including hypertensive, cardiovascular, inflammatory, and diabetic-related diseases. U.S. Patent No. 20140088156 A1, which corresponds to WO 2012/112570 A1, discloses processes for the preparation of EC1728.

International (PCT) Publication Nos. WO 2013/138118 A1, WO 2014/007998 A1, and WO 2017/007548 A1 disclose use as agents for treating inflammatory disorders in non-human mammals such as laminitis in horses, for treating diseases mediated by p21 such as kidney cancer, and for improving podocyte and kidney function and glucose homeostasis in diabetic and pre-diabetic states, respectively. U.S. Pat. Nos. 20160206605 A1 and 20160008342 A1 disclose use as agents for treating respiratory diseases such as cystic fibrosis and for improving cell-based therapy.

In one aspect, the present disclosure discloses a co-crystal compound between a sorafenib derivative and an amino acid. It is desirable to provide drug substances in co-crystalline forms as these can offer an alternative approach to modify or control the physicochemical properties, such as water solubility, of a drug substance. Co-crystallization can also be used to isolate or purify a drug substance during manufacturing.

As used herein the term "obtaining" may include filtration, filtration under vacuum, centrifugation, and decantation for isolation of the product. The product may be preceded for further reaction with or without isolation and with or without drying in case of the product was isolated. As used herein, unless indicated otherwise, the term "isolated" or "isolation" refer to the subject compound as physically separated from the reaction mixture in which it is formed. The term "ambient temperature" and "room temperature" means a temperature range between 20° C. to 40° C.

In one general aspect, there is provided a co-crystal of EC1728 and amino acid of Formula (B)

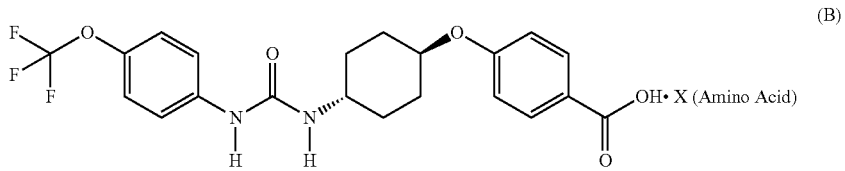

(B)

The said co-crystal can be characterized by its physicochemical parameters, for example those presented hereinafter.

Pharmaceutical co-crystals are crystalline molecular complexes that contain the drug substance along with an additional molecule present in the same crystal structure. The additional molecule or 'guest' has been described in the literature as a co-crystal former. A co-crystal can thus be seen to be a multiple component crystal in which the drug substance and the co-crystal former are arranged in a three-dimensional repetitive structure, wherein non-covalent and non-ion pair interactions exist between the drug substance and the co-crystal former, such as hydrogen bonding, pi-stacking, and van der Waals interactions. Co-crystalline forms show different physicochemical properties compared to the drug substance alone, including melting point, chemical reactivity, apparent solubility, dissolution rate, optical and mechanical properties, vapor pressure, and density. These properties can have a direct effect on the ability to process and/or manufacture a drug substance and the corresponding finalized dosage forms, as well as an effect on drug product stability, dissolution, and bioavailability.

In another aspect, there is provided a process for the preparation of co-crystal of EC1728 and amino acid, the process including: (a) dissolving EC1728 and amino acid in a mixture of ethanol and water to obtain the clear solution; (b) Alternatively adding EC1728 as a powder form in a solution of amino acid in water and washing it with minimum amounts of ethanol to complete dissolution; and (c) removing the solvent to obtain the co-crystal of EC1728 and amino acid.

EC1728 can be prepared by any of the methods described in the literature mentioned herein above. The formation of co-crystal of EC1728 and amino acid can be carried out by using amino acids selected from the group consisting of glycine, L-proline, L-asparagine, L-aspartic acid, L-glutamine, L-glutamic acid, L-lysine, L-arginine, L-histidine, L-serine, L-threonine, L-cysteine, L-methionine, L-phenylalanine, L-tyrosine, L-tryptophan, L-alanine, L-valine, L-leucine, L-isoleucine, D-asparagine, D-aspartic acid, D-glutamine, D-glutamic acid, D-histidine. D-arginine, D-cysteine, D-serine, D-threonine, D-lysine, D-methionine, D-phenylalanine, D-alanine, D-valine, D-leucine, D-isoleucine and D-proline, D-tyrosine, D-tryptophan, and their derivatives with protecting groups such as BOC, Fmoc and etc.

During the process, EC1728 and amino acid can be dissolved in one or more solvents. Both the ingredients may be dissolved in the same solvent, either together or separately in a different solvent. In case of separate dissolution of both ingredients, the two solutions are mixed.

a slight exotherm peaking at 159.9° C. with an integrated area of 11.19 J/g. The exotherm transitioned into two additional endotherms, in which the first peaked at 187.2° C. and the second at 222.4° C. The approximate enthalpies of these events were 13.44 J/g and 137.9 J/g respectively. The DSC signal became noisy possibly due to decomposition and/or reaction. No significant activity was detected on the sample's 1st cooling cycle nor on the sample's 2nd heating and cooling cycles. Upon completion of the measurement, a visible black mass of material was seen on the outside of the crucible above the pierced lid. The sample was re-weighed and found to have lost more than 60% mass.

In another aspect, there is provided a process for the preparation of co-crystal of EC1728 and L-arginine of Formula (C),

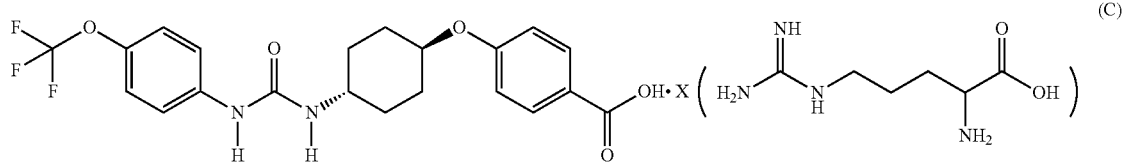
(C)

In general, the solvents are selected from one or more of water, C1-C6 alcohols comprised of methanol, ethanol, isopropanol, n-butanol, and t-butyl alcohol or mixture thereof. In particular, the solvents are methanol and ethanol. After completion of the reaction, the solvent is removed by evaporation or distillation or may be concentrated to obtain the co-crystal.

In another aspect, there is provided a pharmaceutical composition comprising co-crystal of EC1728 and amino acid having one or more pharmaceutically acceptable carriers, excipients and diluents for the treatment of human and animal diseases.

In another aspect, there is provided a co-crystal of EC1728 and L-arginine of Formula (C), the process can include: (a) dissolving EC1728 and L-arginine in a mixture of ethanol and water to obtain the clear solution; (b) Alternatively adding EC1728 as a powder form in a solution of L-arginine in water and washing it with minimum amounts of ethanol to complete dissolution; and (c) removing the solvent to obtain the co-crystal of EC1728 and L-arginine.

In some embodiments, the EC1728 and L-arginine are dissolved in one or more solvents, if desired the reaction mixture may be warmed to obtain complete dissolution. Both the ingredients may be dissolved in the same solvent, either together or separately in a different solvent. In case of separate dissolution of both ingredients, the two solutions are mixed. In some embodiments, the solvent comprises one or more of water, C1-C6-alcohols selected from methanol,

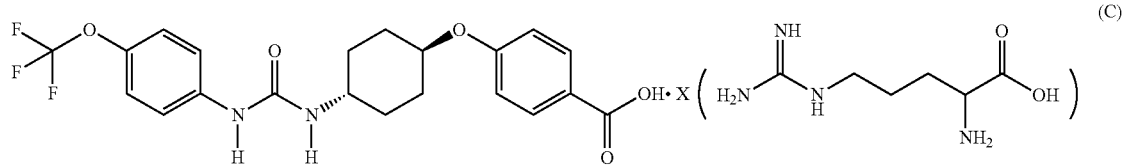
(C)

Figure 1B:
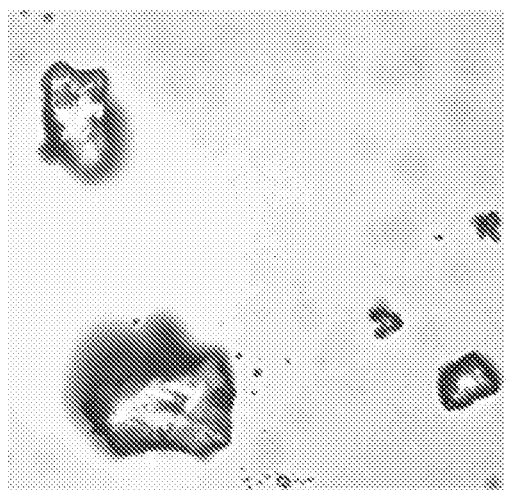
FIG. 1B shows morphology of co-crystal of EC1728 and L-arginine.

FIG. 1A shows morphology of EC1728 compound, while FIG. 1B shows morphology of co-crystal of EC1728 and L-arginine.

Figure 2A:
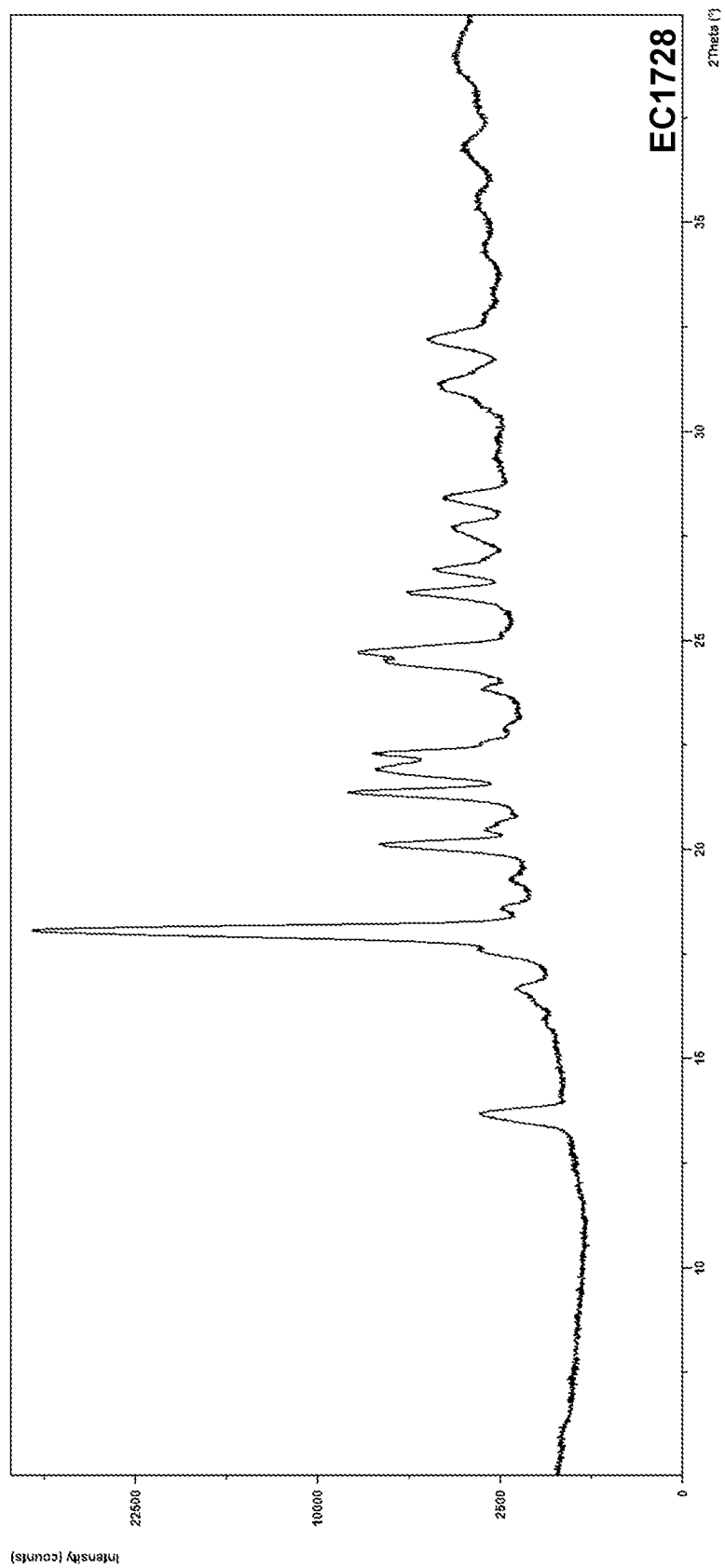
FIG. 2A shows powder x-ray diffraction pattern of EC1728 compound.
Figure 2B:
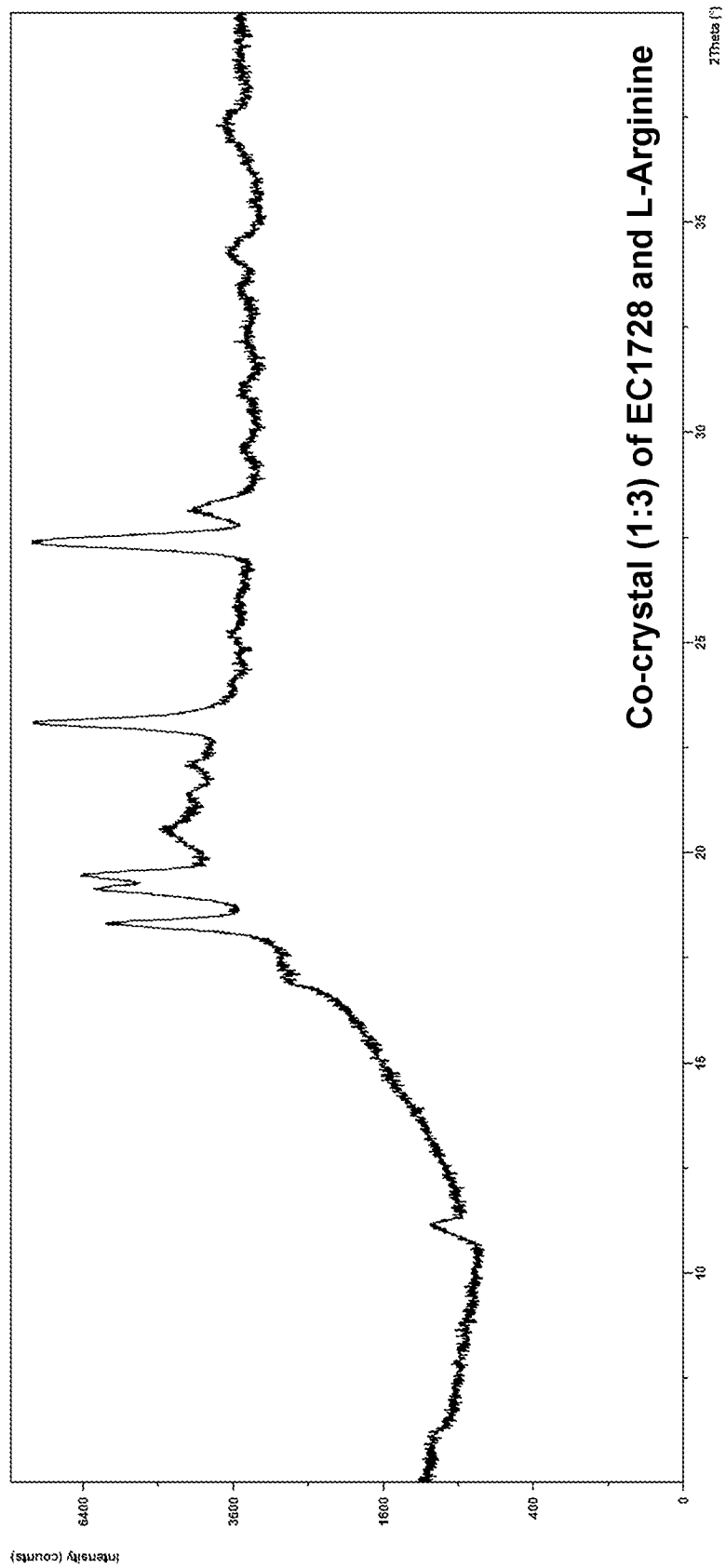
FIG. 2B shows powder x-ray diffraction pattern of co-crystal of EC1728 and L-arginine.
Figure 2C:
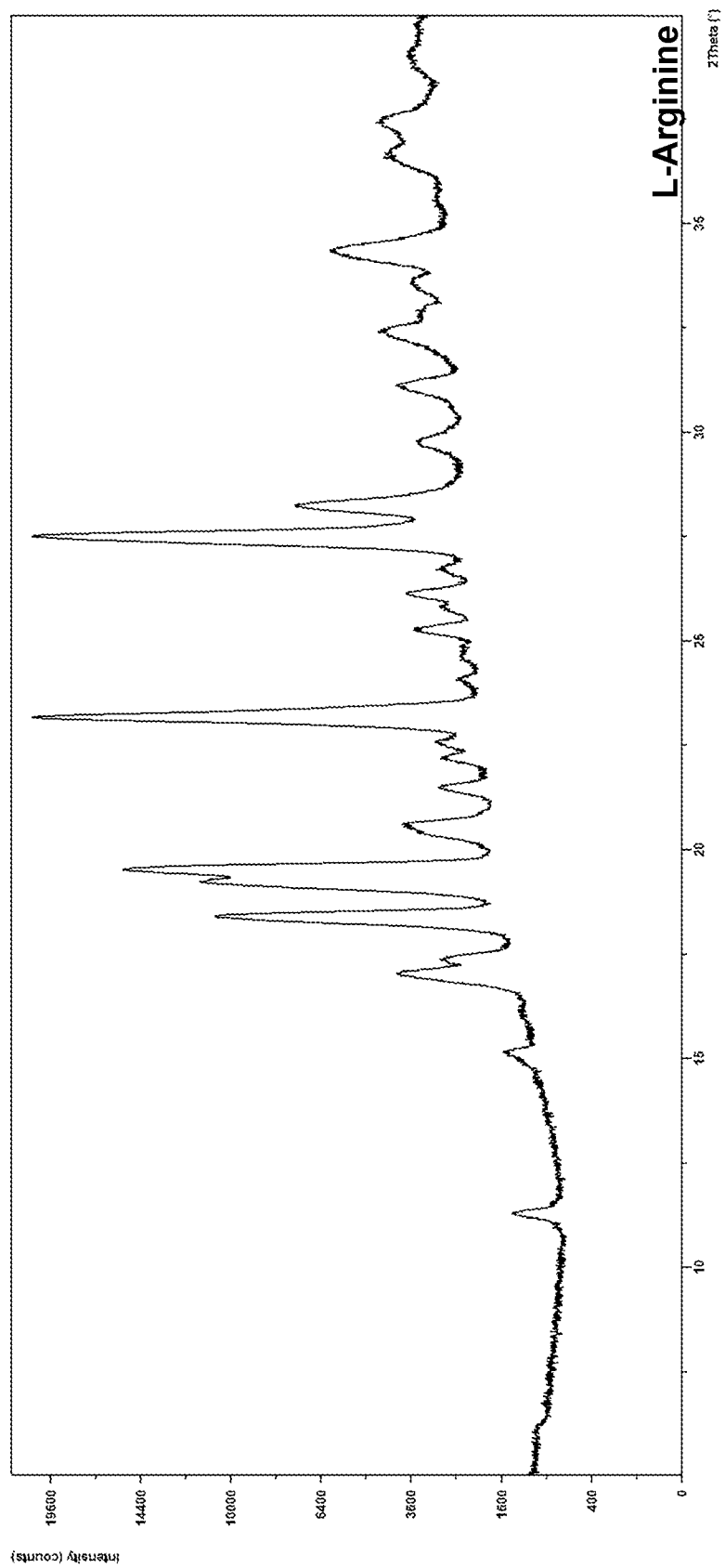
FIG. 2C shows powder x-ray diffraction pattern of L-arginine.

The co-crystal of EC1728 and L-arginine exists as an amorphous form, which is characterized by a powder X-ray diffraction pattern. FIG. 2A shows powder x-ray diffraction pattern of EC1728 compound, FIG. 2B shows powder x-ray diffraction pattern of co-crystal of EC1728 and L-arginine, and FIG. 2C shows powder x-ray diffraction pattern of L-arginine.

Figure 3:
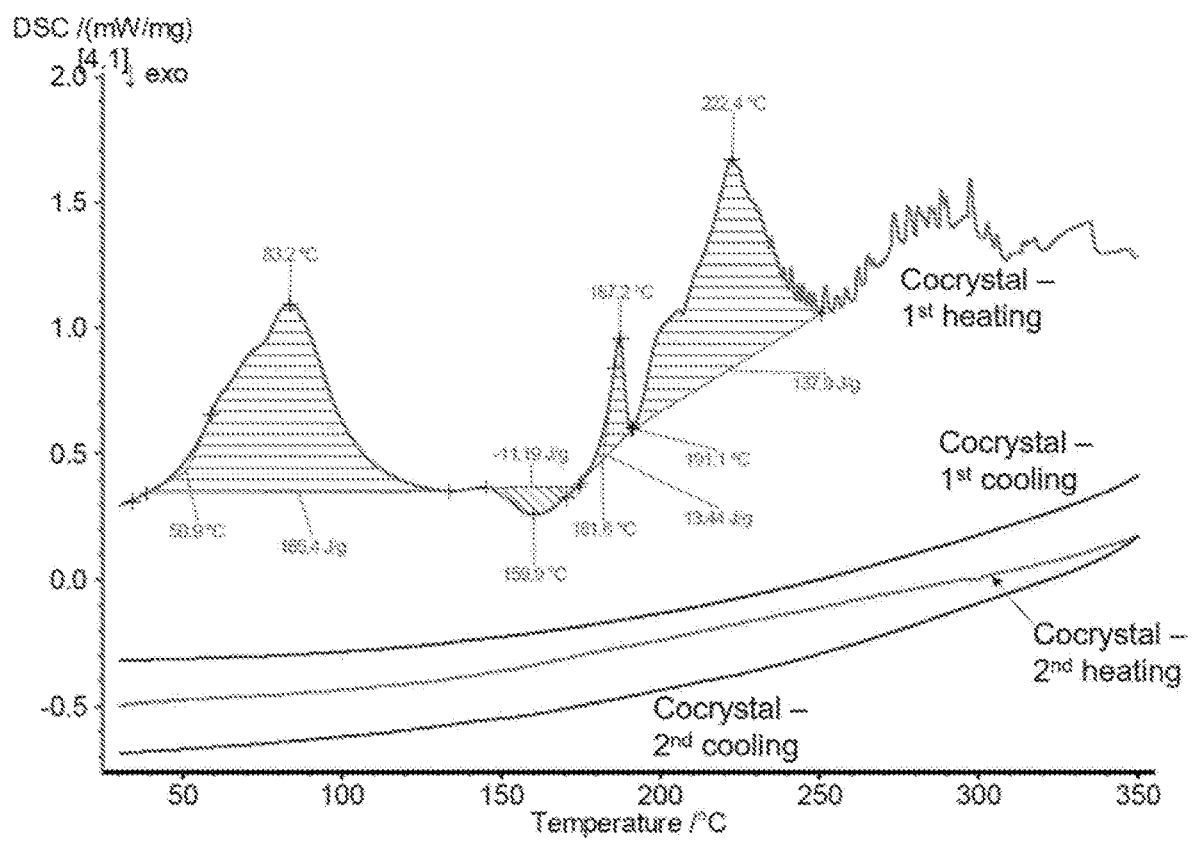
FIG. 3 shows the DSC analysis of the co-crystal of EC1728 and L-arginine.

FIG. 3 shows the DSC analysis of the co-crystal of EC1728 and L-arginine. The DSC thermogram shows that the sample first exhibited an endothermic peak at 83.2° C. with an extrapolated onset temperature of 50.9° C. and an integrated area of 165.4 J/g during the first heating (red). After the initial peak, the sample appears to have exhibited ethanol, isopropanol, n-butyl alcohol, and t-butyl alcohol or mixture thereof. In some embodiments, the EC1728 may be dissolved in a one or more solvent where upon L-arginine is added. The obtained reaction mixture is stirred at room temperature until the complete dissolution is observed. The co-crystal can be obtained after the removal of the solvent by distillation under reduced pressure or the solution is concentrated.

Figure 4A:
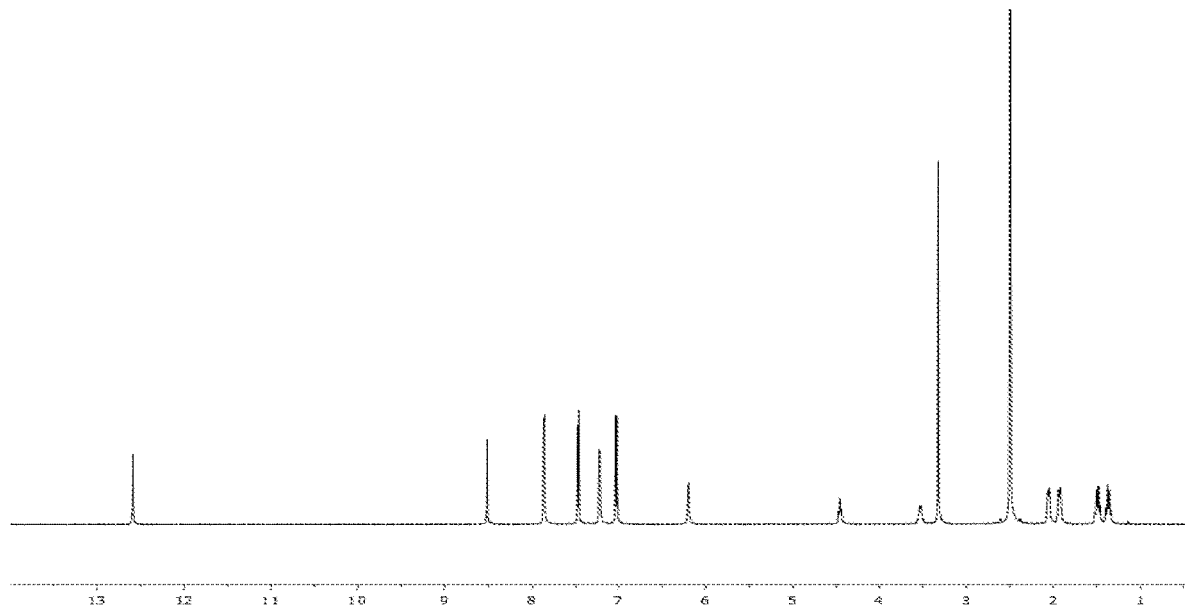
FIG. 4A shows $^1$H NMR spectrum of the EC1728.
Figure 4B:
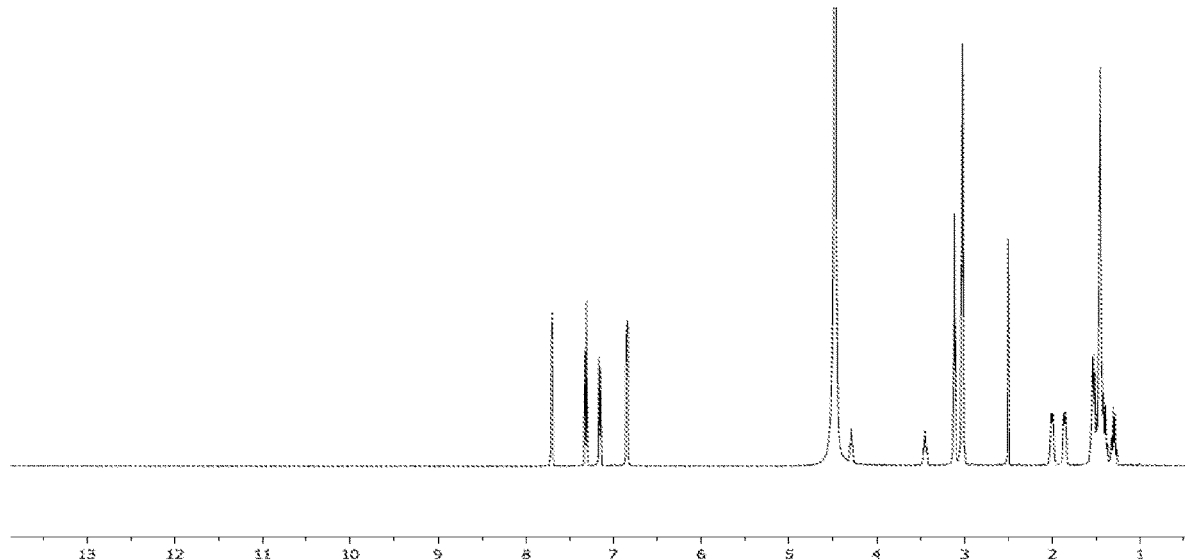
FIG. 4B shows $^1$H NMR spectrum of the co-crystal (1:3) of EC1728 and L-arginine.
Figure 5:
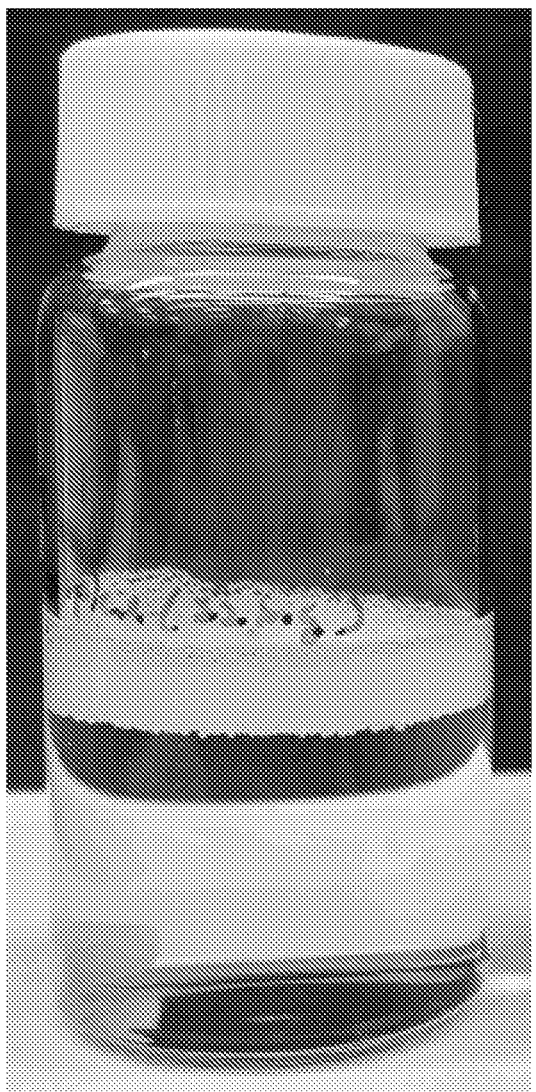
FIG. 5 shows the water solution of the co-crystal (1:3) of EC1728 compound and L-arginine.

FIG. 4A shows $^1$H NMR spectrum of the EC1728 and FIG. 4B shows $^1$H NMR spectrum of the co-crystal (1:3) of EC1728 and L-arginine. Absence of peaks corresponding to the carboxylic acid on the phenyl group ($\delta$ 12.59) and the two amino groups ($\delta$ 8.51 and $\delta$ 6.20) of the urea group on the EC1728 in FIG. 4B suggests that these protons are making interactions with the arginine FIG. 5 shows the improved water solubility of the co-crystal (1:3) of EC1728 compound and L-arginine.

Figure 6:
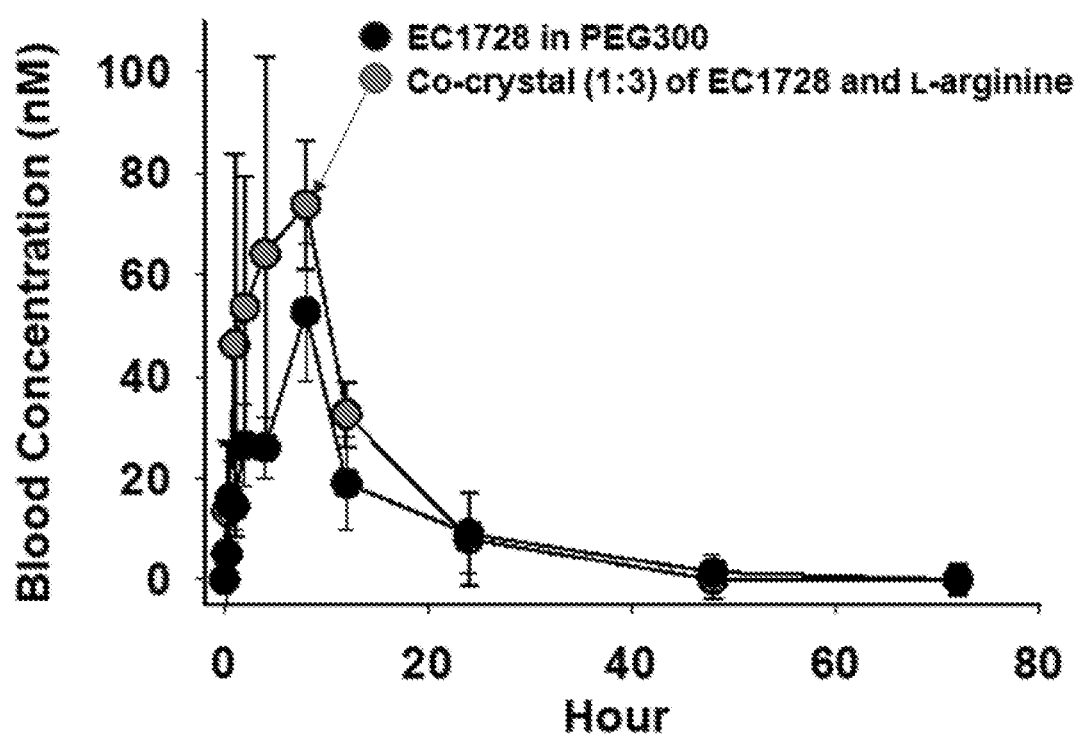
FIG. 6 shows comparison of pharmacokinetic (PK) profiles between EC1728 and the co-crystal of EC1728 and L-arginine when administered by oral gavage.

FIG. 6 shows comparison of pharmacokinetic (PK) profiles between EC1728 and the co-crystal of EC1728 and L-arginine when administered by oral gavage.

Figure 7A:
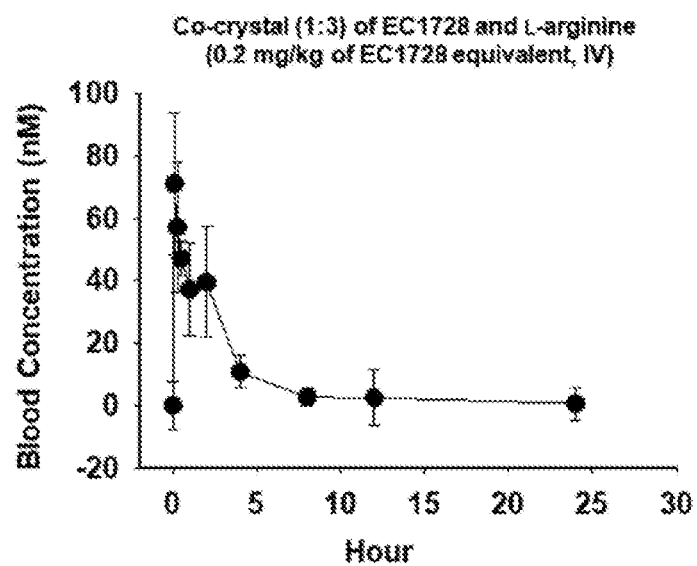
FIG. 7 shows comparison of pharmacokinetic (PK) profiles between co-crystal (1:3) of EC1728 and L-arginine and co-crystal (1:10) of EC1728 and L-arginine when administered by iv injection.
Figure 7B:
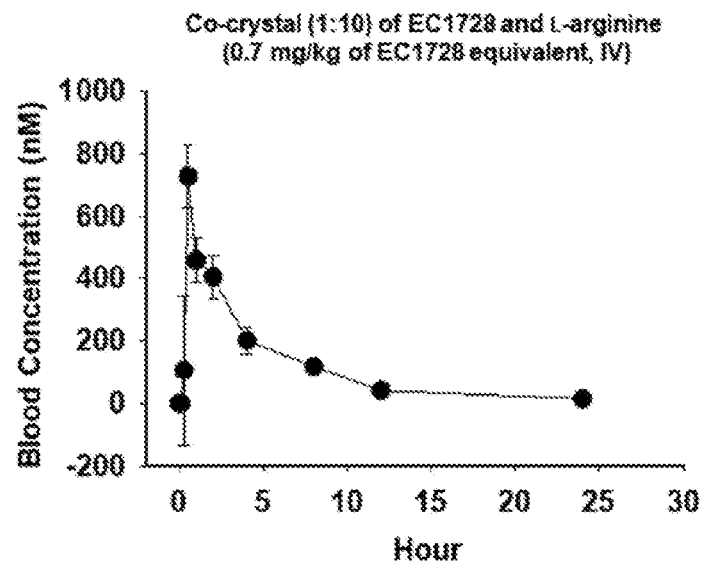

FIG. 7 shows comparison of pharmacokinetic (PK) profiles between co-crystal (1:3) of EC1728 and L-arginine and co-crystal (1:10) of EC1728 and L-arginine when administered by iv injection.

In some embodiments, there is provided a pharmaceutical composition comprising co-crystal of EC1728 and L-arginine having one or more pharmaceutically acceptable carriers, excipients and diluents for the treatment of human and animal diseases. These drug products are different because the active ingredient is present in a lower energy, amorphous crystalline form that has desirable intrinsic properties such as water solubility. The co-crystal has better flow properties, is easier to prepare, shows better water solubility comparable to the EC1728. The pharmaceutically acceptable excipients comprise one or more of surfactants, solubilizers, disintegrants, microcrystalline cellulose, starch, sodium starch glycolate, crosslinked carboxy methyl cellulose sodium, crosslinked PVP, pigments, flavors, fillers, lubricants, glidants, preservatives, thickening agents, buffering agents and pH modifiers. The examples are set forth to aid in understanding the disclosure but are not intended to and should not be construed to; limit its scope in any way. The examples do not include detailed descriptions of conventional methods. Such methods are well known to those of ordinary skill in the art and are described in numerous publications.

Presented below are examples discussing the design and evaluation of efficacy of new anaerobic digestion system for treating wastewater. The following examples are provided to further illustrate the embodiments of the present disclosure but are not intended to limit the scope of the disclosure. While they are typical of those that might be used, other procedures, methodologies, or techniques known to those skilled in the art may alternatively be used.

EXAMPLES

Example 1

Co-Crystal (1:3) of EC1728 and L-Arginine

To a solution of L-arginine (0.12 g, 0.68 mmol, 3 equiv) in 10 mL of water, EC1728 (0.1 g, 0.23 mmol) was added at room temperature. After adding 10 mL of EtOH, the reaction mixture was stirred for 10 minutes to obtain a clear solution. The solvent was removed in vacuo (extra EtOH may be required to remove water completely by forming an azeotrope and this process can be repeated). The resulting solid was dried at room temperature for 12 hours in a vacuum oven to get 0.22 g of co-crystal of EC1728 and L-arginine.

Example 2

Co-Crystal (1:x) of EC1728 and L-Arginine

To a solution of L-arginine (x equiv, x≥3) in 10 mL of water, EC1728 (0.1 g, 0.23 mmol) was added at room temperature. After adding 10 mL of EtOH, the reaction mixture was stirred for 10 minutes to obtain a clear solution. The solvent was removed in vacuo. (extra EtOH may be required to remove water completely by forming an azeotrope and this process can be repeated). The resulting solid was dried at room temperature for 12 hours in a vacuum oven to get co-crystal (1:x) of EC1728 and L-arginine.

Example 3

Characterization of the Co-Crystal Samples

The X-ray powder diffraction pattern was measured under the following experimental conditions. Instrument: X'Pert Pro MRD; Make: PANanalytical; X-Ray: Cu/45kv/40Ma; Divergence slit: 1"; Scattering Slit: 1"; Receiving Slit: ½"; Monochromator: none; Counter: Scintillation Counter Scan Mode: Continuous; Time per step: 1 s; Sampling Width (step size): 0.01°; Scan Axes: 2Theta-Omega; Scan Range: 5.0° to 40.0°; Omega Offset: 0.00°.

Differential scanning calorimetric analysis may be performed using a NETZSCH DSC 214 Polyma. 2-5 mg samples were placed in crimped aluminum pans and heated from 20° C. to 350° C. and cooled from 350° C. to 20° C. in a nitrogen atmosphere at a heating rate of 10° C./min.

Those skilled in the art will recognize, or be able to ascertain, using no more than routine experimentation, numerous equivalents to the specific composition and procedures described herein. Such equivalents are considered to be within the scope of this disclosure and are covered by the following claims.

The $^1$H NMR spectrum was measured by Varian VNMRS 600 MHz spectrometer wherein samples were dissolved in 1:1 DMSO-$d_6$/$D_2$O for analysis.

Those skilled in the art will recognize, or be able to ascertain, using no more than routine experimentation, numerous equivalents to the specific composition and procedures described herein. Such equivalents are considered to be within the scope of this disclosure and are covered by the following claims.

What is claimed is:

1. A co-crystal compound having Formula (II):

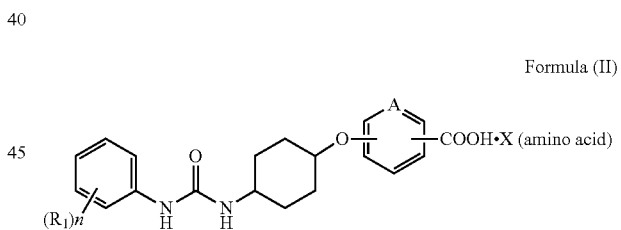

Formula (II)

or a stereoisomer thereof,
wherein:
A is CH or N;
n is an integer selected from 0-5;
$R_1$ is selected from the group consisting of H, halogen, hydroxyl, $N_3$, $NH_2$, $NO_2$, $CF_3$, $OCF_3$, $C_{1-10}$alkyl, substituted $C_{1-10}$alkyl, $C_{1-10}$alkoxy, substituted $C_{1-10}$alkoxy, acyl, acylamino, acyloxy, acyl $C_{1-10}$alkyloxy, amino, substituted amino, aminoacyl, aminocarbonyl, $C_{1-10}$alkyl, aminocarbonylamino, aminodicarbonylamino, aminocarbonyloxy, and aminosulfonyl;
X is an integer selected from 3-20;
the amino acid is selected from the group consisting of glycine, L-proline, L-asparagine, L-aspartic acid, L-glutamine, L-glutamic acid, L-lysine, L-arginine, L-histidine, L-serine, L-threonine, L-cysteine, L-methionine, L-phenylalanine, L-tyrosine, L-tryptophan, L-alanine, L-valine, L-leucine, L-isoleucine, D-asparagine, D-aspartic acid, D-glutamine, D-glutamic acid, D-histidine, D-arginine, D-cysteine, D-serine, D-threonine, D-lysine, D-methionine, D-phenylalanine, D-alanine, D-valine, D-leucine, D-isoleucine and D-proline, D-tyrosine, D-tryptophan, and their derivatives with protecting groups.

2. The co-crystal compound of claim 1, with the structure of Formula (B)

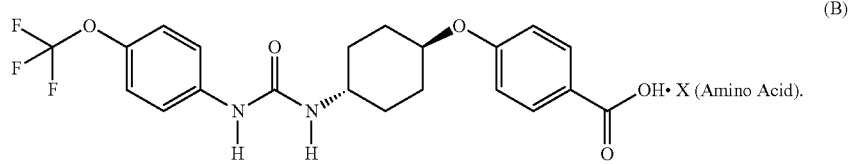

3. The co-crystal compound of claim 2, with the structure of Formula (C)

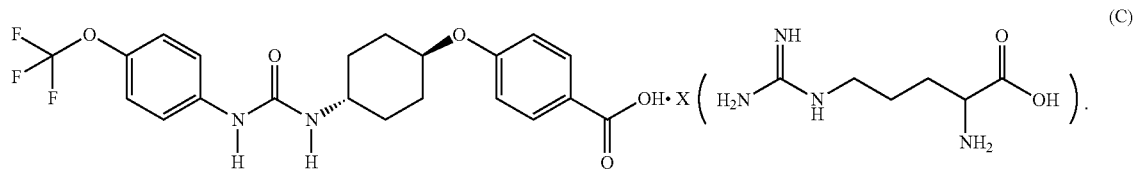

4. The co-crystal compound of claim 1, wherein the amino acid is L-arginine.

5. The co-crystal compound of claim 1, which is soluble in a pharmaceutically acceptable aqueous vehicle to form an orally deliverable solution.

6. A pharmaceutical composition comprising the co-crystal compound of claim 1 having one or more pharmaceutically acceptable carriers, excipients and diluents.

7. The pharmaceutical composition of claim 6, which is in a form of a rapidly disintegrating tablet.

8. The pharmaceutical composition of claim 6, wherein the pharmaceutically acceptable excipient is selected from the group consisting of surfactants, solubilizers, disintegrants, microcrystalline cellulose, starch, sodium starch glycolate, crosslinked carboxy methyl cellulose sodium, crosslinked PVP, pigments, flavors, fillers, lubricants, glidants, preservatives, thickening agents, buffering agents, pH modifiers and any combination thereof.

9. A method of treating or preventing a disease or disorder in a subject by inhibiting soluble epoxide hydrolase (sEH), the method comprising administering to the subject a pharmaceutical composition comprising: (a) a compound of claim 1; and (b) a pharmaceutically acceptable carrier.

10. A method of treating or preventing a disease or disorder in a subject by inhibiting soluble epoxide hydrolase (sEH), the method comprising: (a) dissolving, in a pharmaceutically acceptable aqueous vehicle, a compound of claim 1 to form an aqueous pharmaceutical composition; and (b) administering the pharmaceutical composition to the subject.

11. The method of claim 9, wherein the compound is a co-crystal of EC1728 and L-arginine.

12. The method of claim 9, wherein the pharmaceutical composition is administered orally or intravenously.

13. The method of claim 9, wherein the disease or disorder is selected from the group consisting of renal, hepatic, or pulmonary hypertension, chronic pain, acute pain, inflammation, renal inflammation, hepatic inflammation, vascular inflammation, and lung inflammation, adult respiratory distress syndrome, diabetic complications, end stage renal disease, Raynaud syndrome, arthritis, myocardial infarction, stroke, ischemia, Alzheimer's disease, Parkinson's disease, Gehrig's disease (Amyotrophic Lateral Sclerosis), Huntington's disease, Multiple Sclerosis, senile dementia, subcortical dementia, arteriosclerotic dementia, AIDS-associated dementia, other dementias, cerebral vasculitis, epilepsy, Tourette's syndrome, Guillain Bane Syndrome, Wilson's disease, Pick's disease, encephalitis, encephalomyelitis, meningitis, prion diseases, cerebellar ataxias, cerebellar degeneration, spinocerebellar degeneration syndromes, Friedrich's ataxia, ataxia telangiectasia, spinal dysmyotrophy, progressive supranuclear palsy, dystonia, muscle spasticity, tremor, retinitis pigmentosa, striatonigral degeneration, mitochondrial encephalomyopathies and neuronal ceroid lipofuscinosis.

14. The method of claim 9, wherein the subject is a human or non-human mammal.

15. The method of claim 9, wherein the subject is an equine and the disease or disorder is pain, inflammation or laminitis.

16. A process for preparing a compound of claim 1, comprising: (a) dissolving a sorafenib derivative and an amino acid in a mixture of ethanol and water to obtain a solution; and (b) removing the water and ethanol to obtain a co-crystal.

17. A process for preparing a compound of claim 1, comprising: (a) adding a sorafenib derivative in a dried form to a solution of an amino acid and water and washing it with ethanol to complete dissolution; and (b) removing the water and ethanol to obtain a co-crystal.

* * * * *